US011701688B2

(12) United States Patent
Dacruz et al.

(10) Patent No.: US 11,701,688 B2
(45) Date of Patent: Jul. 18, 2023

(54) METHODS AND SYSTEMS FOR MULTI-FREQUENCY TRANSDUCER ARRAY FABRICATION

(71) Applicant: GE Precision Healthcare LLC, Milwaukee, WI (US)

(72) Inventors: Edouard Dacruz, Nice (FR); Flavien Daloz, Antibes (FR); Jason Barrett, Queen Creek, AZ (US)

(73) Assignee: GE Precision Healthcare LLC, Milwaukee, WI (US)

( * ) Notice: Subject to any disclaimer, the term of this patent is extended or adjusted under 35 U.S.C. 154(b) by 536 days.

(21) Appl. No.: 16/700,903

(22) Filed: Dec. 2, 2019

(65) Prior Publication Data

US 2021/0162460 A1 Jun. 3, 2021

(51) Int. Cl.
*B06B 1/06* (2006.01)
*B06B 1/02* (2006.01)
*A61B 8/00* (2006.01)
*H10N 30/03* (2023.01)
*H10N 30/20* (2023.01)

(52) U.S. Cl.
CPC .......... *B06B 1/0269* (2013.01); *A61B 8/4494* (2013.01); *B06B 1/0607* (2013.01); *B06B 1/0614* (2013.01); *H10N 30/03* (2023.02); *A61B 8/4488* (2013.01); *B06B 2201/76* (2013.01); *H10N 30/20* (2023.02)

(58) Field of Classification Search
CPC . B06B 1/0614; B06B 1/0607; B06B 2201/76; B06B 1/0269; H01L 41/09
See application file for complete search history.

(56) References Cited

U.S. PATENT DOCUMENTS

| | | | |
|---|---|---|---|
| 9,061,320 B2* | 6/2015 | Hajati | B06B 1/0629 |
| 9,660,170 B2* | 5/2017 | Hajati | H01L 41/042 |
| 2002/0042577 A1 | 4/2002 | Hatangadi | |
| 2007/0193354 A1 | 8/2007 | Felix et al. | |
| 2012/0176002 A1* | 7/2012 | Kim | H04R 3/04 |
| | | | 310/317 |
| 2018/0098750 A1 | 4/2018 | Haider et al. | |
| 2018/0169701 A1 | 6/2018 | Daloz et al. | |
| 2018/0175278 A1 | 6/2018 | Daloz et al. | |

FOREIGN PATENT DOCUMENTS

WO 2017089376 A1 6/2017

OTHER PUBLICATIONS

Dacruz, E. et al., "Methods and Systems for a Multi-Frequency Transducer Array," U.S. Appl. No. 16/700,916, filed Dec. 2, 2019, 74 pages.

(Continued)

*Primary Examiner* — J. San Martin
(74) *Attorney, Agent, or Firm* — McCoy Russell LLP

(57) ABSTRACT

Various methods and systems are provided for a multi-frequency transducer array. In one example, the transducer array is fabricated by forming an interdigitated structure from a first comb structure with a first sub-element and a second comb structure with a second sub-element. The interdigitated structure is coupled to a base package, a matching layer, and a backing layer to form a plurality of multi-frequency transducers.

7 Claims, 28 Drawing Sheets

(56) References Cited

OTHER PUBLICATIONS

Dacruz, E. et al., "Methods and Systems for Wafer Scale Transducer Array Fabrication," U.S. Appl. No. 16/701,048, filed Dec. 2, 2019, 74 pages.
Dacruz, E. et al., "Methods and Systems for Ground Recover in a Transducer Array," U.S. Appl. No. 16/700,886, filed Dec. 2, 2019, 74 pages.
International Application No. PCT/US2020/062303 filed Nov. 25, 2020—International Search Report and Written Opinion dated Jul. 1, 2021; 19 pages.

* cited by examiner

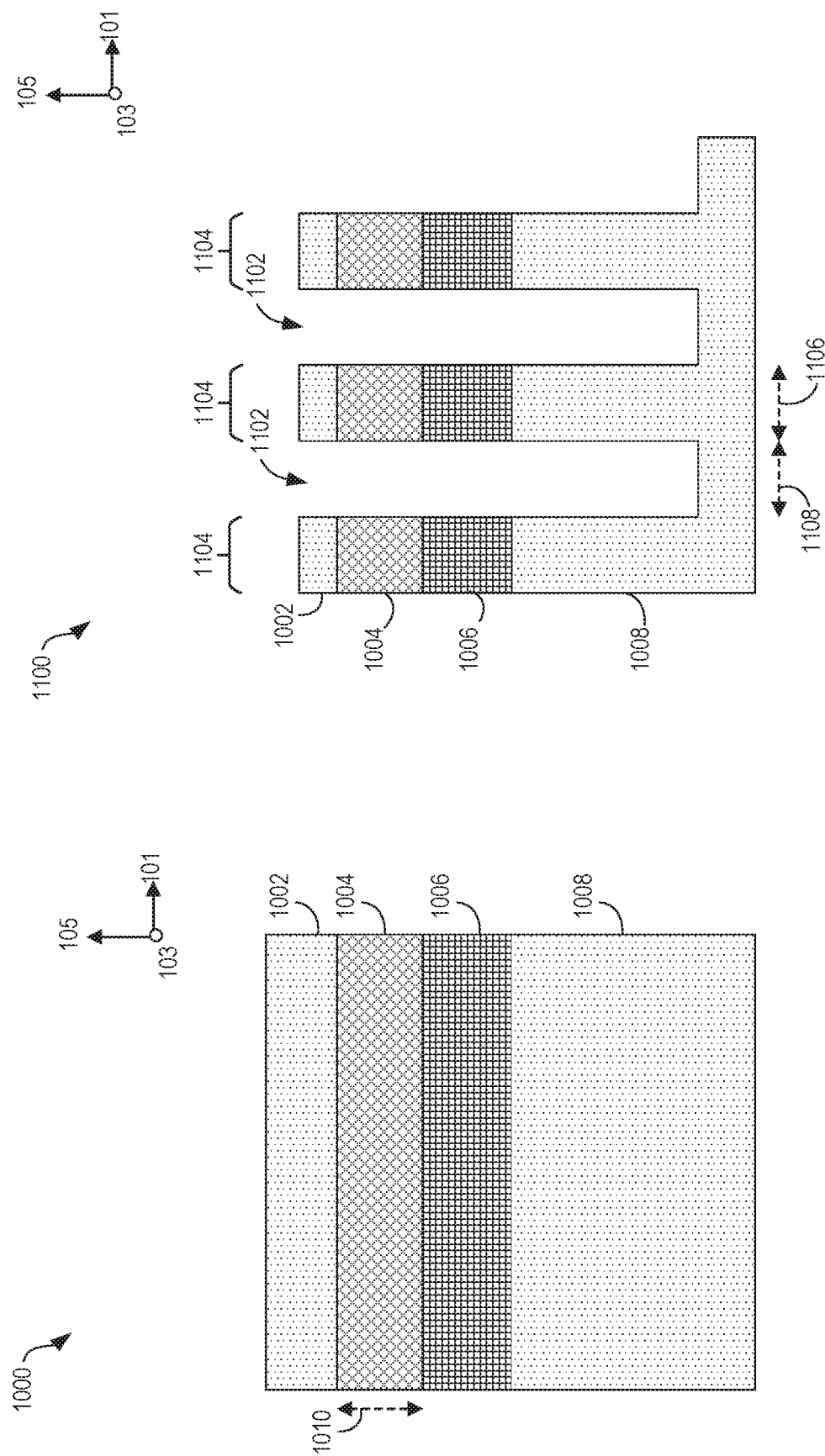

METHODS AND SYSTEMS FOR MULTI-FREQUENCY TRANSDUCER ARRAY FABRICATION

FIELD

Embodiments of the subject matter disclosed herein relate to a transducer for a medical device.

BACKGROUND

Transducer probes are used in a variety of applications to convert energy from a physical form to an electrical form. For example, a transducer probe may include piezoelectric materials which generate electrical voltage from a mechanical stress or strain exerted on the materials. Piezoelectric transducer probes are configured to be highly sensitive to provide large signal amplitudes, broad bandwidth for use across a wide range of frequencies, and short-duration impulse for high axial resolution. Such properties are desirable for medical applications such as imaging, non-destructive evaluation, fluid flow sensing, etc. Furthermore, frequency apodization of the transducer probe may mitigate loss of signal resolution due to signal attenuation and dispersion as the signal travels away from its source.

BRIEF DESCRIPTION

In one embodiment, a method includes forming a first comb structure with a first sub-element having a first resonance frequency, forming a second comb structure, complementary in geometry to the first comb structure with a second sub-element having a second resonance frequency, combining the first and second comb structures to form an interdigitated structure, forming a third acoustic stack by coupling the interdigitated structure to a base package, and coupling the third acoustic stack to a matching layer block and a back layer block to form a plurality of multi-frequency transducers. In this way, a transducer array may be fabricated via an approach that allows a frequency range of the transducer array to be adjusted.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below:

FIG. 10 shows a first example of an acoustic stack block.

FIG. 11 shows a first comb structure formed from the acoustic stack block of FIG. 10.

DETAILED DESCRIPTION

Figure 1:
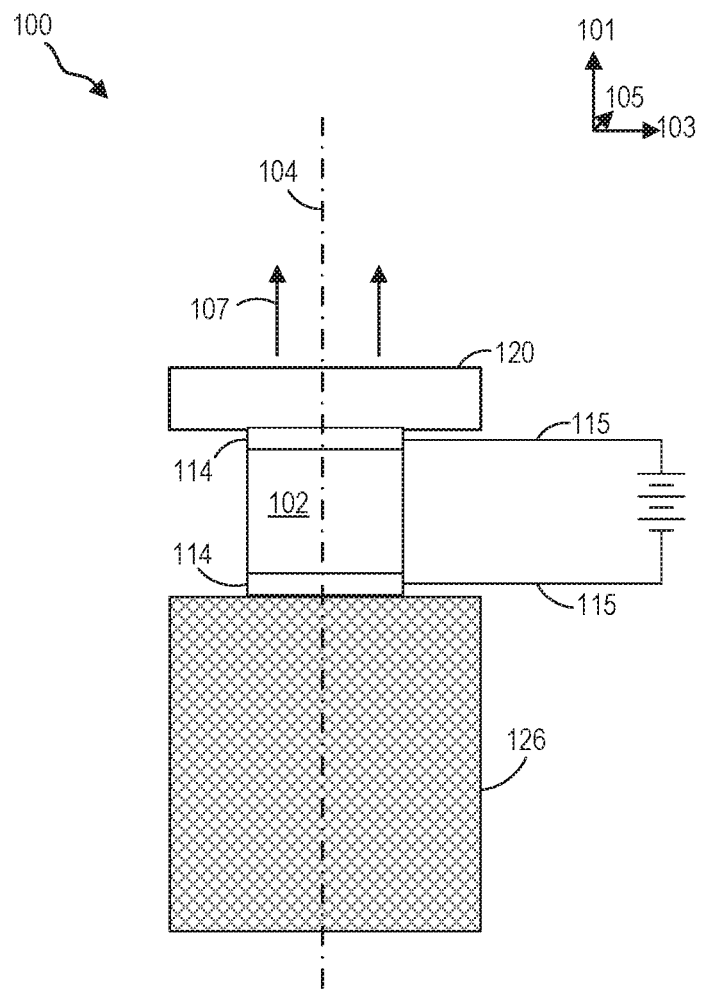
FIG. 1 shows an example of an acoustic stack of an ultrasound transducer.
Figure 2:
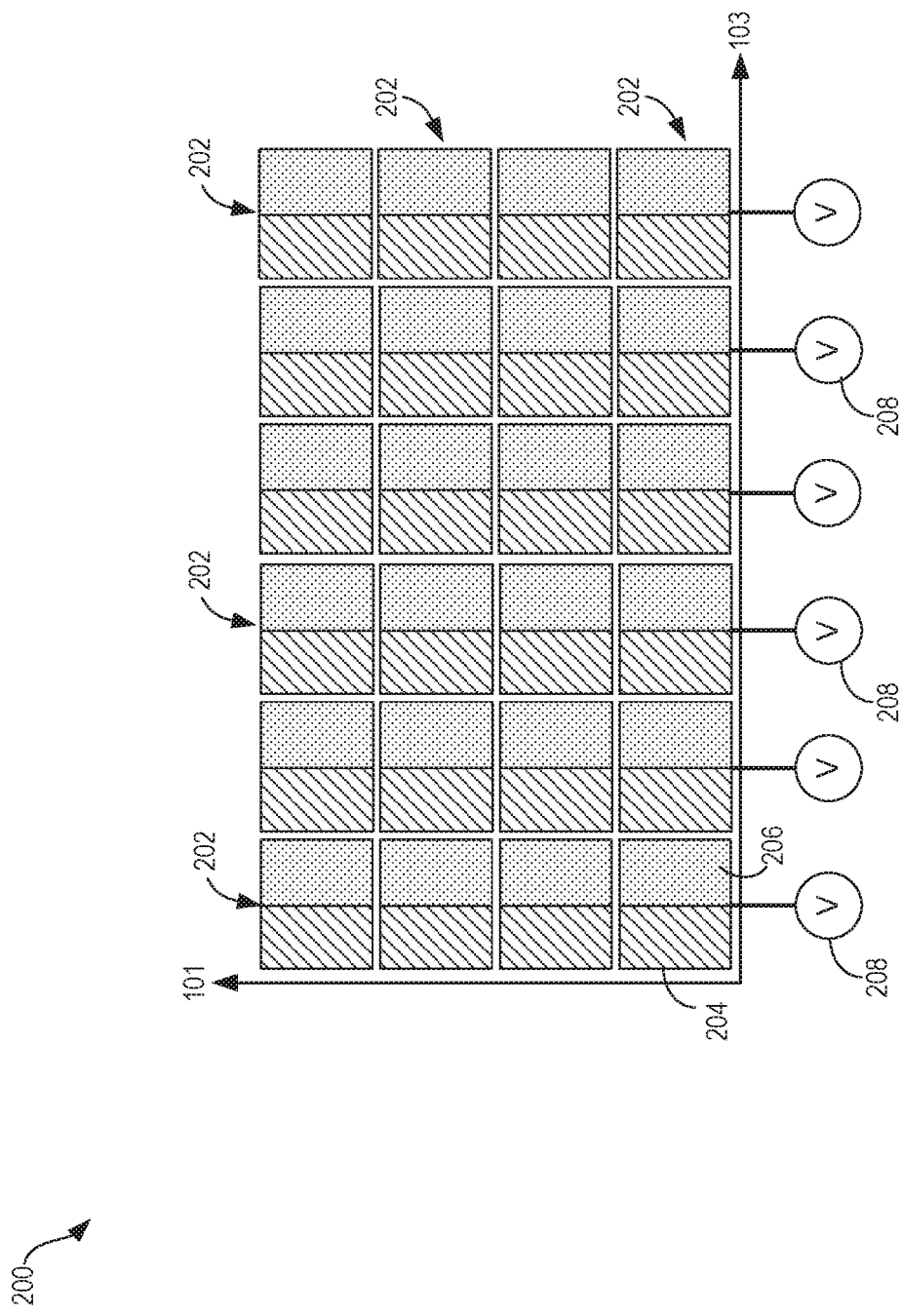
FIG. 2 shows an example of a homogeneous multi-element transducer array.
Figure 3:
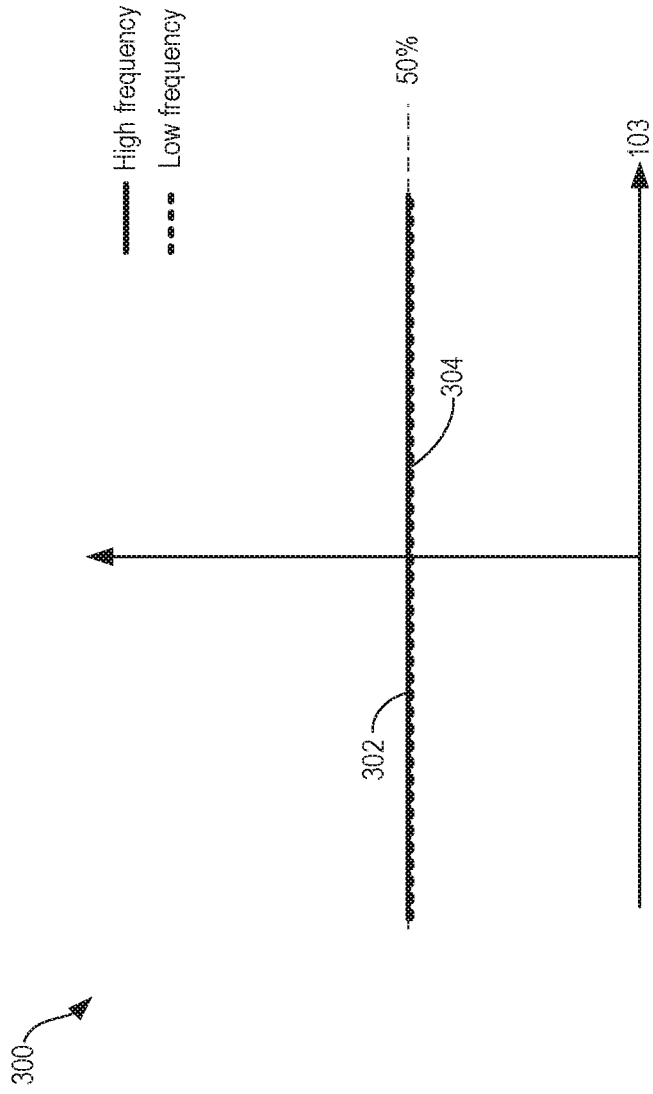
FIG. 3 shows a first graph of an apodization function along an elevation direction provided by the multi-element transducer array of FIG. 2.
Figure 4:
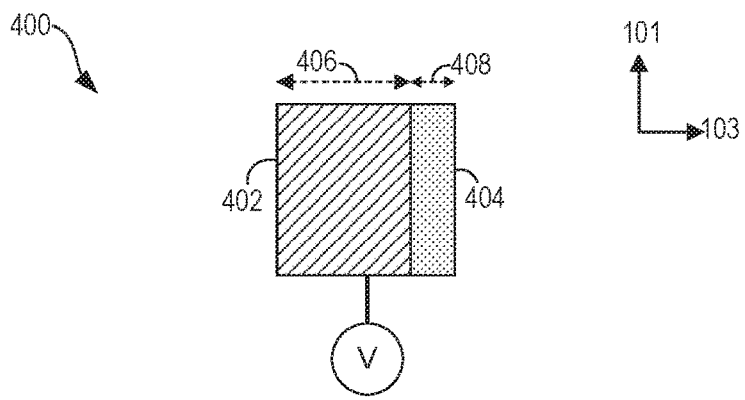
FIG. 4 shows a first example of a piezoelectric element formed of two sub-elements.
Figure 5:
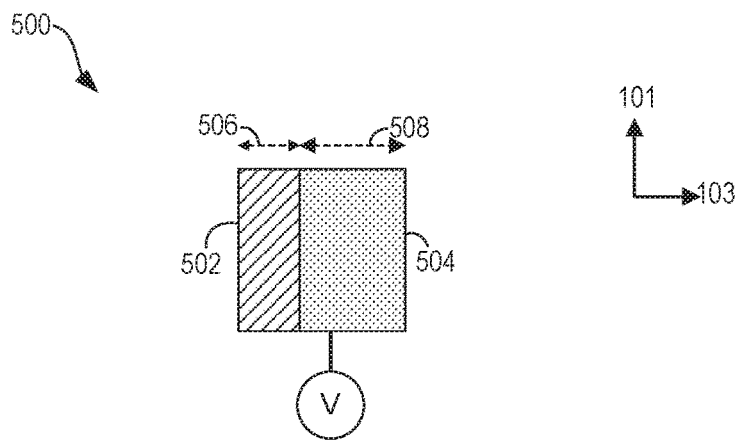
FIG. 5 shows a second example of a piezoelectric element formed of two sub-elements.
Figure 6:
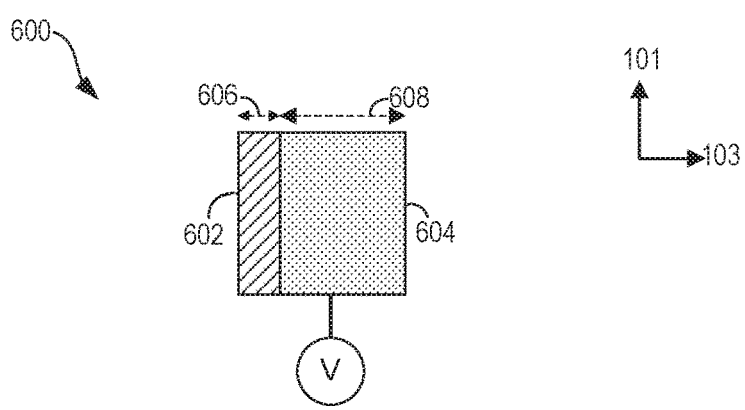
FIG. 6 shows a third example of a piezoelectric element formed of two sub-elements.
Figure 7:
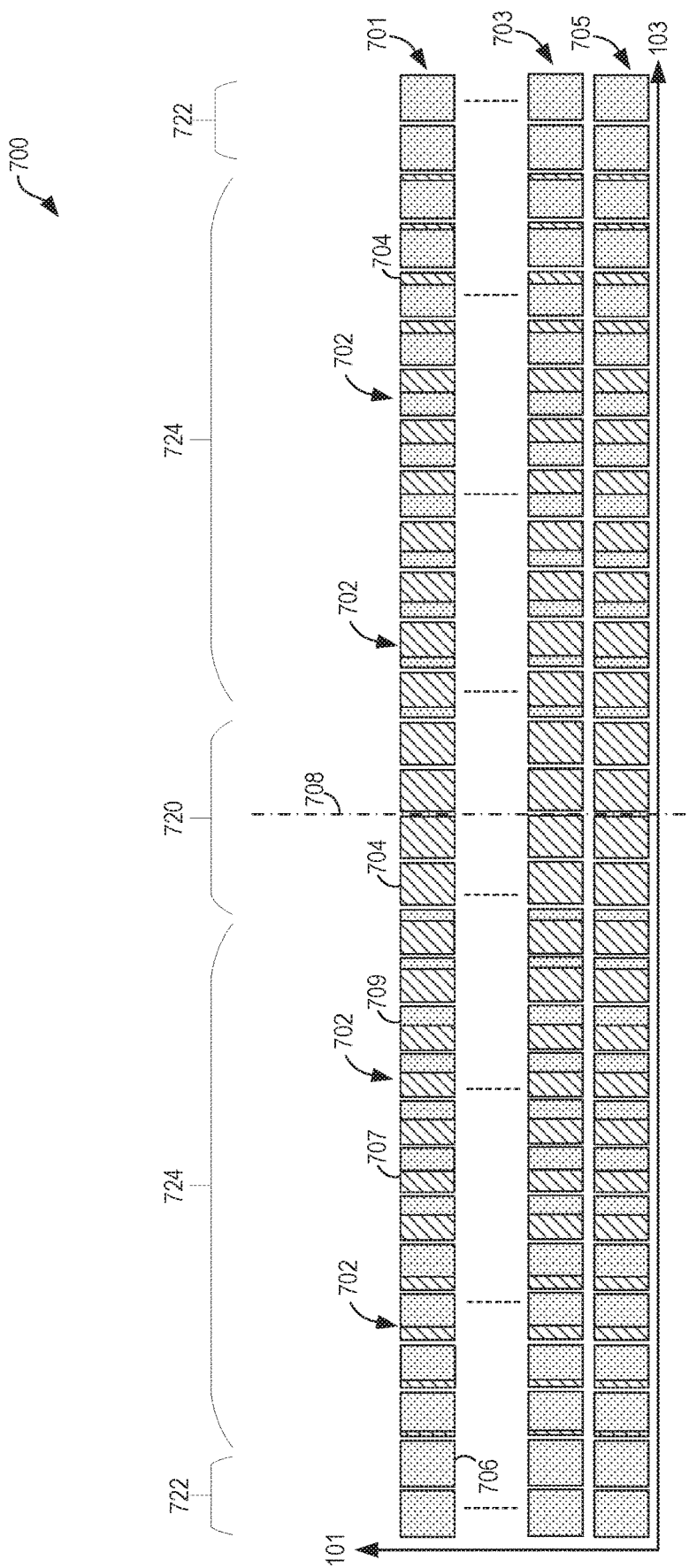
FIG. 7 shows a first example of a multi-element transducer array with varying spatial frequency distribution.
Figure 8:
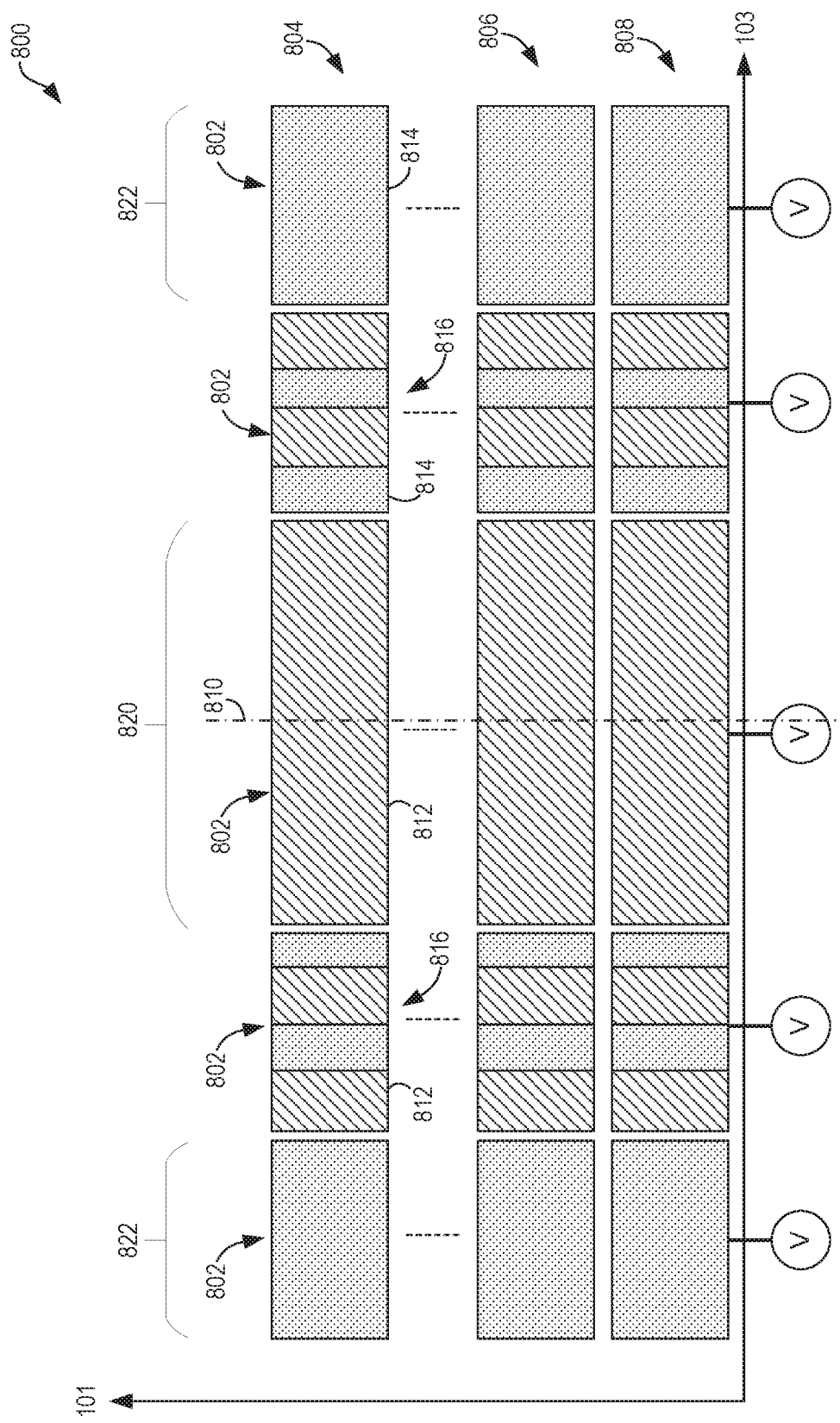
FIG. 8 shows a second example of a multi-element transducer array with varying spatial frequency distribution.
Figure 9:
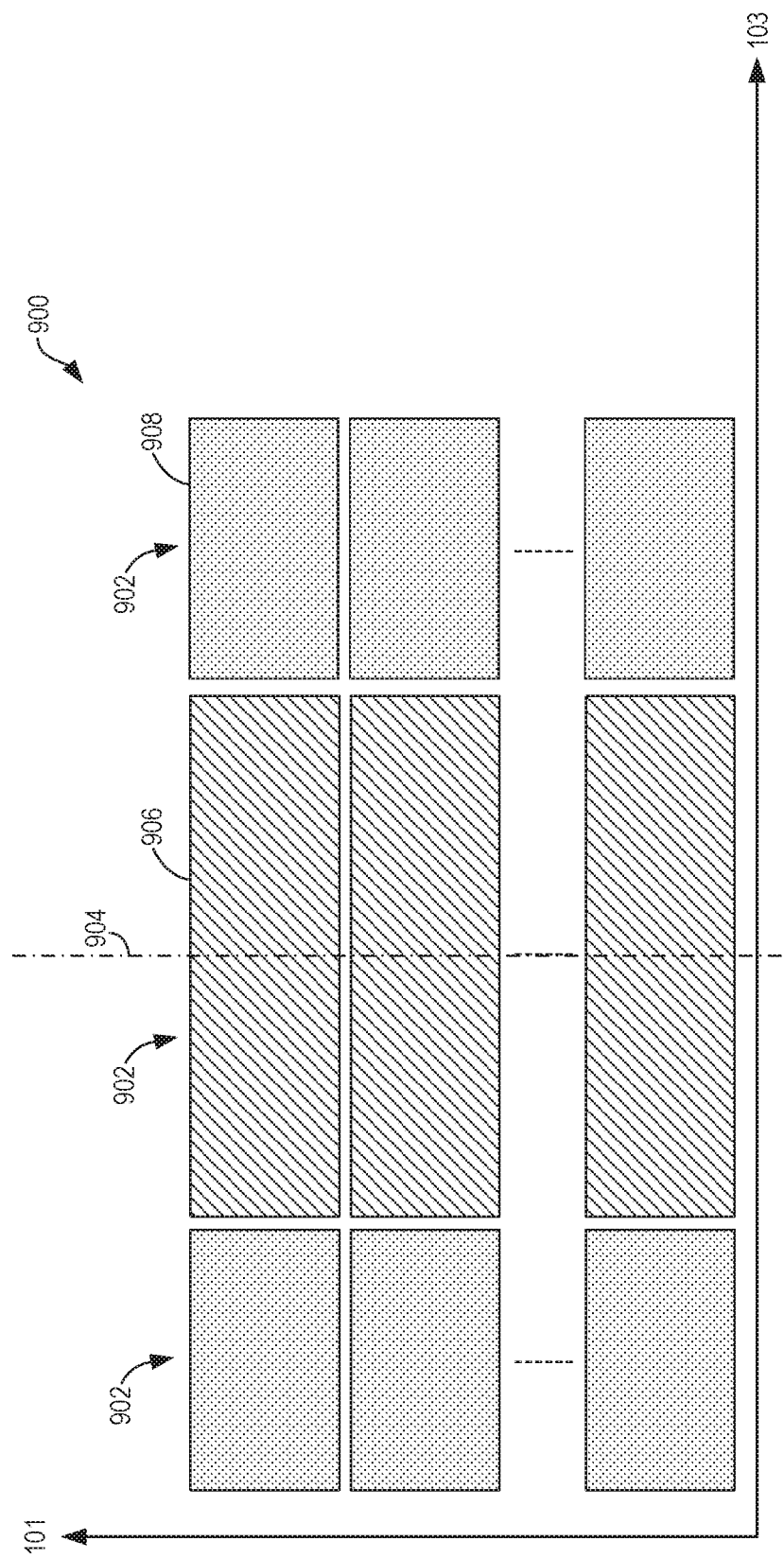
FIG. 9 shows a third example of a multi-element transducer array with varying spatial frequency distribution.
Figure 36:
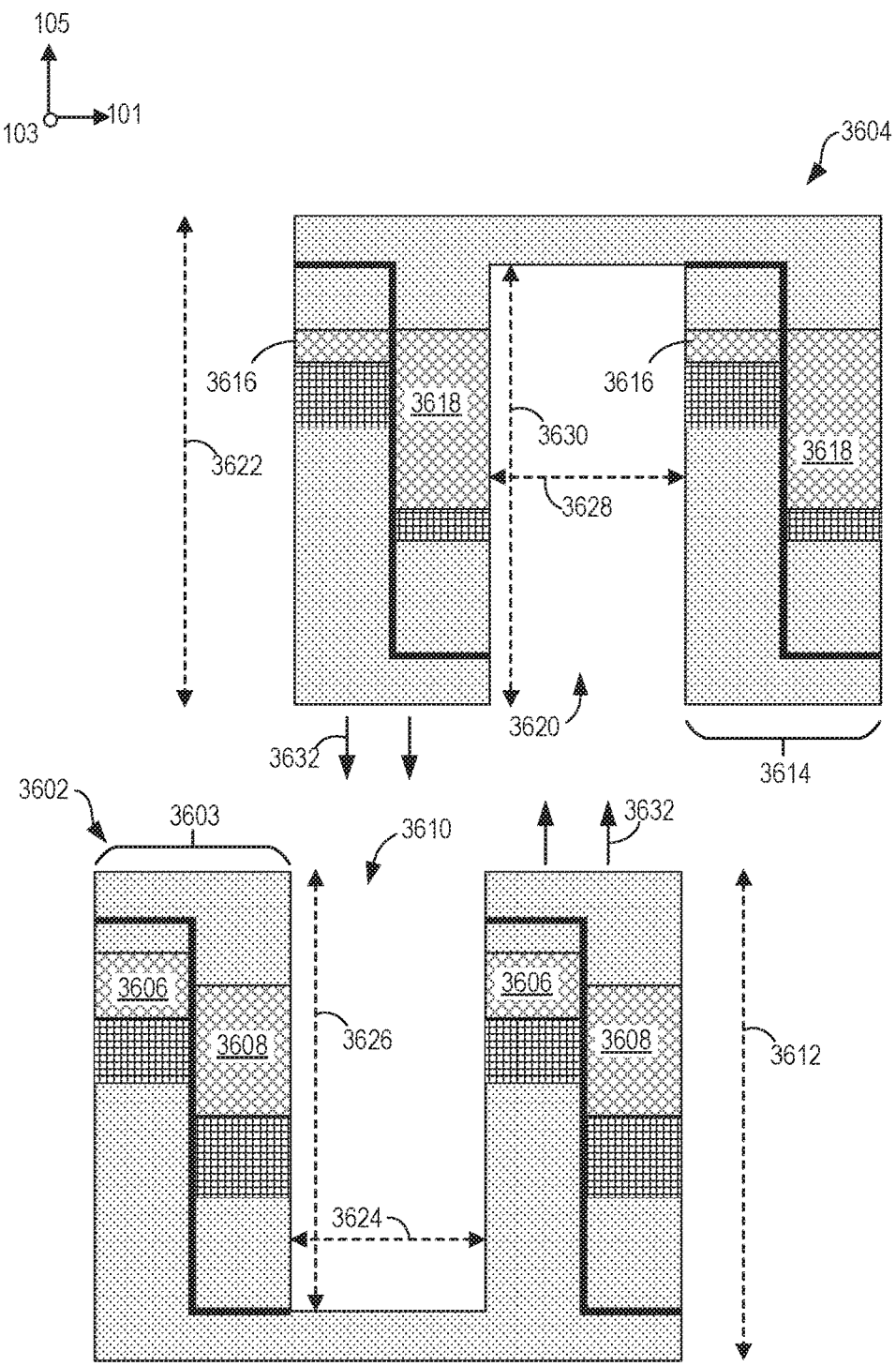
FIG. 36 shows a combining of two multi-element comb structures to form an acoustic stack with four sub-elements.
Figure 37:
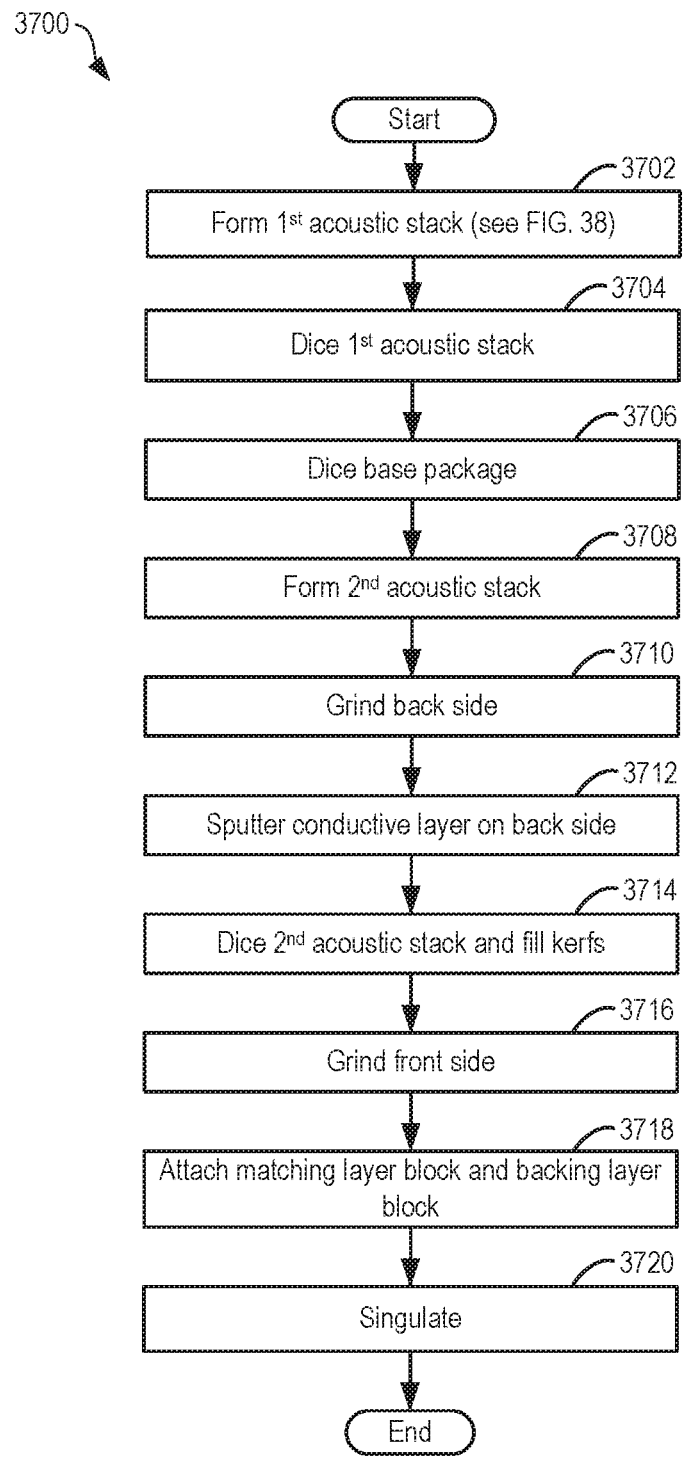
FIG. 37 shows an example of a routine for fabricating a multi-frequency acoustic stack.
Figure 38:
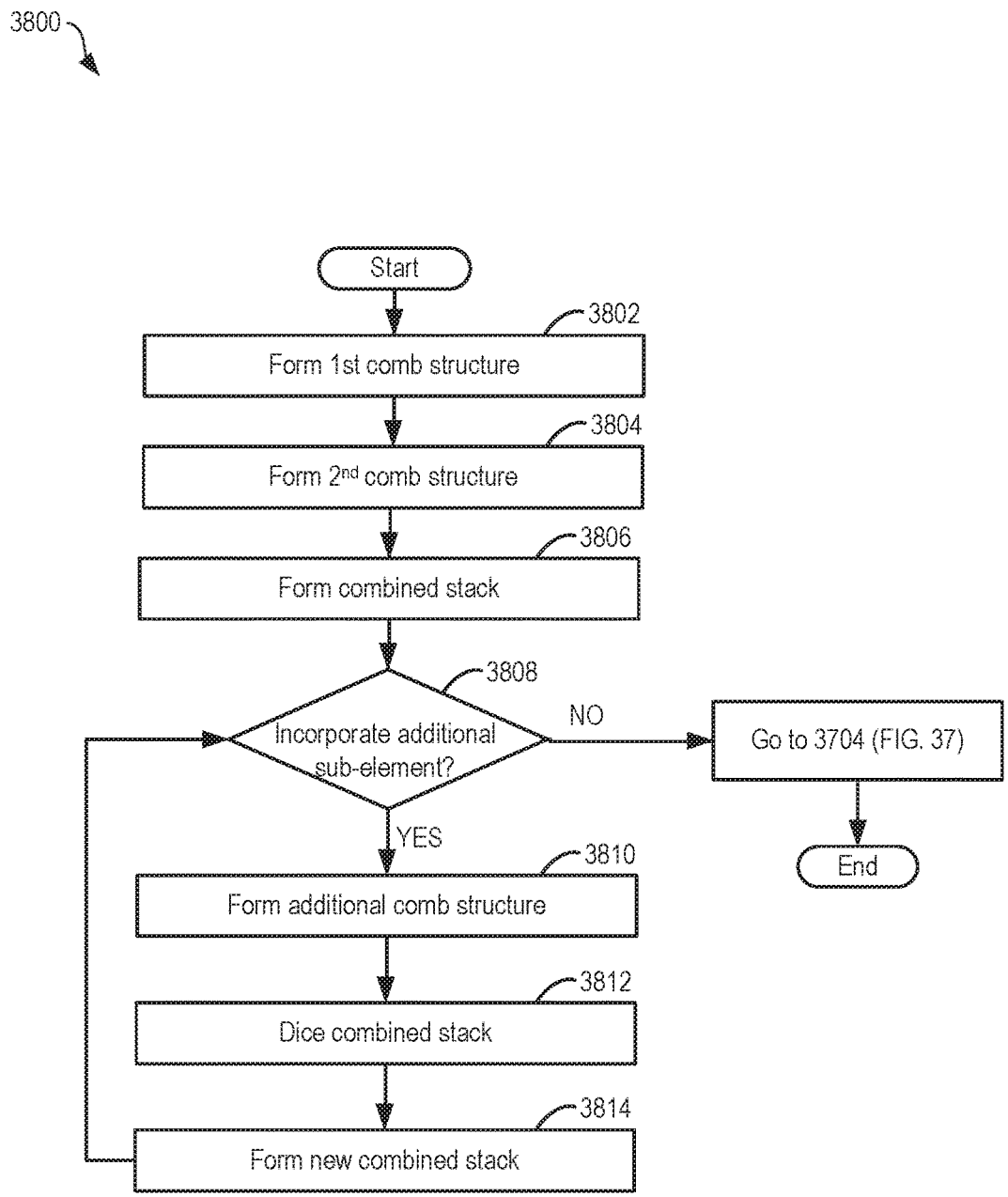
FIG. 38 shows an example of a method for forming multi-frequency elements for the acoustic stack that may be executed as part of the routine of FIG. 37.
Figure 39:
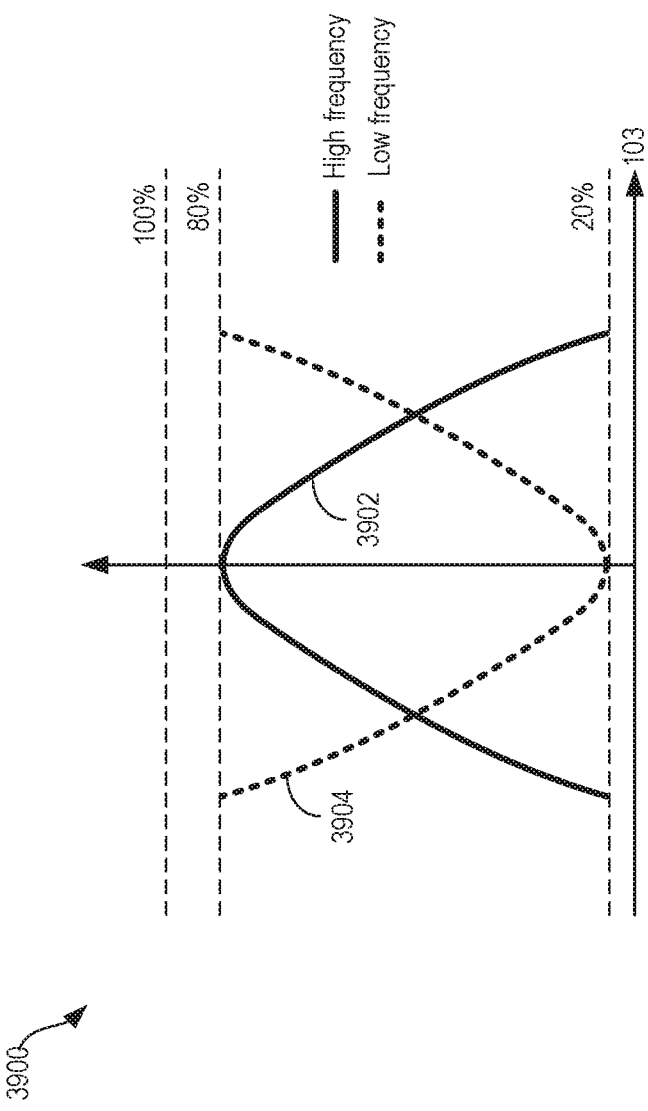
FIG. 39 shows a second graph of an apodization function along an elevation direction provided by a multi-element transducer array with non-homogeneous spatial frequency distribution.

The following description relates to various embodiments of an acoustic stack for a transducer probe. The acoustic stack may be configured with a broad frequency bandwidth by adapting the acoustic stack with a piezoelectric element formed from more than one sub-element. An example of an acoustic stack for a transducer probe is shown in FIG. 1. Each of the more than one sub-element may be a different type of element with a different resonance frequency. Relative proportions of the more than one sub-element may be maintained constant along both an azimuth direction and an elevation direction of the transducer probe to form a homogeneous array. An example of a homogeneous multi-frequency transducer array is depicted in FIG. 2 and a first graph showing a frequency apodization function provided by the homogeneous multi-element (e.g., more than one sub-element) array is illustrated FIG. 3. In contrast, a tapered apodization function is shown in FIG. 39 which may be produced by a multi-frequency transducer array with varying percent content of sub-elements included in each element of the transducer array. As described above, relative proportions of the sub-elements forming the piezoelectric element may be varied, as shown in FIGS. 4-6. In some examples, a multi-frequency transducer array may not be homogeneous along at least one of the azimuth and elevation directions, instead exhibiting a varying spatial frequency distribution. Examples of different spatially distributed multi-frequency transducer arrays are shown in FIGS. 7-9. A multi-element transducer array may be fabricated via a wafer scale approach to enable scalable, low cost manufacturing. Various processes included in the wafer scale approach are depicted in FIGS. 10-36 and 40-42. An example of a first routine for fabricating a multi-frequency acoustic stack for a transducer probe by the wafer scale approach is shown in FIG. 37. An example of a second routine for forming multi-frequency elements for the acoustic stack is depicted in FIG. 38 and may be included in the first routine of FIG. 37.

FIGS. 1-2, 4-36, and 40-42 show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space there-between and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

Piezoelectric elements may be implemented in transducer probes for a wide range of medical applications, including imaging, non-destructive testing, diagnosis, measuring blood flow, etc. The piezoelectric elements may be formed of a class of crystalline materials that become electrically polarized when subjected to a mechanical strain. When stressed, the piezoelectric elements output a voltage that is proportional to the applied stress.

A piezoelectric transducer probe, e.g., a device utilizing a piezoelectric effect to convert energy from one form to another, may offer high sensitivity, high frequency response and high transient response. In some examples, such as in ultrasound transducer probes, a converse piezoelectric effect may be leveraged where electricity is applied to the piezoelectric elements, causing deformation of the material and generation of ultrasonic waves. As such, an external, mechanical force is not demanded and the piezoelectric transducer probe may be packaged as a compact, easily transportable device.

Although the piezoelectric transducer probe is a highly sensitive instrument, an operational frequency bandwidth of the probe may be narrow. For example, the piezoelectric material may be associated with a low frequency, e.g., between 0.5-2.25 MHz, or a high frequency, e.g., between 15.0-25.0 MHz, but not both. Similarly, the transducer probe may be adapted for transmitting or receiving but may not be equipped for high performance in both applications due to a focused frequency range of the particular type of piezoelectric material. Broadband transducer probes may provide wider operational frequency ranges but adapting the probes with electrical impedance matching may be challenging and cost prohibitive.

In one example, the issues described above may be addressed by a piezoelectric transducer probe adapted with a multi-frequency transducer array. The multi-frequency transducer array may include elements in each transducer that are formed from more than one sub-element, each sub-element having a different resonance frequency. In other words, each element may be a hybrid element with an overall resonance frequency modified by the resonance frequencies of the sub-elements. Thus, configuring the transducer array with hybrid elements of varying compositions may enable the transducer array operate across a range of frequencies while maintaining a sensitivity and resolution of a multi-frequency transducer probe in which the transducer array is implemented. Furthermore, the transducers may be fabricated via a wafer level approach that provides ground recovery, frequency apodization, and frequency agility in both the azimuth and elevation directions. A spatial frequency distribution may thereby be controlled and the transducers may be manufactured through a cost-effective, scalable manner.

Multi-frequency piezoelectric transducers, as described herein, may be used in a variety of medical devices. For example, as shown in FIG. 1, a piezoelectric transducer may be included in an ultrasound probe, used to create an image based on ultrasonic signals. It will be appreciated that the ultrasound probe is a non-limiting example of a medical device utilizing the piezoelectric transducer and incorporation of the piezoelectric transducer in other medical devices have been envisioned. For example, the piezoelectric transducer may be used to convert energy in non-destructive testers, Jetter systems, high voltage power sources, etc. The following description of FIG. 1 is an exemplary overview of how the piezoelectric transducer may be implemented in the ultrasound transducer probe.

An ultrasound probe includes one or more active components for generating an ultrasonic signal. An example of an active component, or piezoelectric element 102 of an ultrasound probe is shown in a schematic diagram of an acoustic stack 100 in FIG. 1, with a central axis 104. A set of reference axes are provided, indicating an azimuth direction 101, an elevation direction 103, and a transverse direction 105 perpendicular to both the azimuth and elevation directions. In other examples, the set of reference axes may represent a z-axis 101, an x-axis 103, and a y-axis 105. The piezoelectric element 102 is shown in FIG. 1 with the central axis 104 parallel with the azimuth direction 101.

It will be noted that while the acoustic stack 100 is shown configured for a linear ultrasound probe and the azimuth direction is described as parallel with the z-axis in FIG. 1, other examples may include an azimuth direction that is angled relative to the z-axis, depending on a shape of a piezoelectric element array. For example, the ultrasound probe may be curvilinear or phased array, thus generating non-linear beams that are not parallel with the z-axis.

While a single piezoelectric element is shown in FIG. 1, the ultrasound probe may include a plurality of piezoelectric elements arranged in an array and individually coupled to an electrical energy source by wires. Each electrical circuit formed of one or more piezoelectric elements may be a transducer. In some examples, the transducer may include an array of piezoelectric elements which may arranged in a variety of patterns, or matrices, including one-dimensional (1D) linear, two-dimensional (2D) square, 2D annular, etc. In one example, the transducer may be formed from more than one type of piezoelectric element, thereby providing a multi-frequency piezoelectric transducer. A frequency distribution along each of the azimuth and elevation directions may adapted to be uniform or non-uniform. Further details of the multi-frequency piezoelectric transducer are provided below, with reference to FIGS. 2-42.

Each transducer may be electrically insulated from adjacent transducers but may all be coupled to common layers positioned above and below the piezoelectric element, with respect to the azimuth direction. The plurality of piezoelectric elements and accompanying layers may be enclosed by an outer housing of the ultrasound probe which may be, for example, a plastic case with a variety of geometries. For example, the outer housing may be a rectangular block, a cylinder, or a shape configured to fit into a user's hand comfortably. As such, components shown in FIG. 1 may be adapted to have geometries and dimensions suitable to fit within the outer housing of the ultrasound probe.

The piezoelectric element 102 may be a block formed of a natural material such as quartz, or a synthetic material, such as lead zirconate titanate, that deforms and vibrates when a voltage is applied by, for example, a transmitter. In some examples, the piezoelectric element 102 may be a single crystal with crystallographic axes, such as lithium niobate and PMN-PT $(Pb(Mg_{1/3}Nb_{2/3})O_3-PbTiO_3)$. The vibration of the piezoelectric element 102 generates an ultrasonic signal formed of ultrasonic waves that are transmitted out of the ultrasound probe in a direction indicated by arrows 107, e.g., along the azimuth direction 101. The piezoelectric element 102 may also receive ultrasonic waves, such as ultrasonic waves reflected from a target object, and convert the ultrasonic waves to a voltage. The voltage may be transmitted to a receiver of the ultrasound imaging system and processed into an image.

Electrodes 114 may be in direct contact with the piezoelectric element 102 to transmit the voltage via wires 115, the voltage converted from ultrasonic waves. The wires 115 may be connected to a circuit board (not shown) to which a plurality of wires from electrodes of the plurality of piezoelectric elements may be fixed. The circuit board may be coupled to a coaxial cable providing electronic communication between the ultrasound probe and the receiver.

An acoustic matching layer 120 may be arranged above the piezoelectric element 102, with respect to the azimuth direction 101, oriented perpendicular to the central axis 104. The acoustic matching layer 120 may be a material positioned between the piezoelectric element 102 and a target object to be imaged. By arranging the acoustic matching layer 120 in between, the ultrasonic waves may first pass through the acoustic matching layer 120, and emerge from the acoustic matching layer 220 in phase, thereby reducing a likelihood of reflection at the target object. The acoustic matching layer 220 may shorten a pulse length of the ultrasonic signal, thereby increasing an axial resolution of the signal.

A backing 126 may be arranged below the piezoelectric element 102, with respect to the z-axis. In some examples, the backing 126 may be a block of material that extends along the elevation direction 103 so that each of the plurality of piezoelectric elements in the ultrasound probe are directly above the backing 126, with respect to the azimuth direction 101. The backing 126 may be configured to absorb ultrasonic waves directed from the piezoelectric element 102 in a direction opposite of the direction indicated by arrows 107 and attenuate stray ultrasonic waves deflected by the outer housing of the ultrasound probe. A bandwidth of the ultrasonic signal, as well as the axial resolution, may be increased by the backing 126.

A piezoelectric transducer (PZT) probe may provide high penetration into a target as well as high frequency and transient responses, enabling high resolution data to be obtained. However, a type of piezoelectric element included in the probe may operate within a frequency bandwidth that constrains use of the probe to a particular application. For example, probe with a low central frequency piezoelectric element may be used to produce ultrasound images of deep tissues or organs but may not provide sufficient flaw resolution or thickness measurement capabilities. Thus, use of piezoelectric transducer probes for a variety of applications may demand access to multiple probes with different piezoelectric elements.

In contrast, a capacitive micromachined ultrasonic transducer (CMUT) probe, when used in ultrasonic applications, may offer broader bandwidth as well as more efficient fabrication, due to construction of the CMUTs on silicon via micromachining techniques. The broader CMUT bandwidth enables the CMUT probes to achieve greater axial resolution than the PZT probe. However, a sensitivity and penetration of the CMUT probe may be less than the PZT probe. Furthermore, CMUTs may be more prone to acoustic crosstalk than PZTs.

In one example, high penetration and broad bandwidth may be provided in a PZT probe by adapting the PZT probe with transducers equipped with piezoelectric elements formed from more than one type of sub-element, each sub-element being a different type of piezoelectric material. By combining piezoelectric sub-elements with different resonance frequencies into one transducer, an array of multi-frequency piezoelectric elements may be provided. Each of the multi-frequency elements may have a distinct frequency, depending on relative proportions of the sub-elements, allowing the multi-frequency elements to transmit and receive signals over a wider range of frequencies in comparison to a single element transducer probe.

For example, as shown in FIG. 2, an example of a first matrix 200 with multi-frequency elements may be a homogeneous bi-dimensional array, such as a butterfly-type matrix array, with homogeneous multi-frequency elements 202. The first matrix 200 may represent an arrangement of the elements 202 within a transducer of an acoustic stack, such as the acoustic stack 100 of FIG. 1. At least one of the acoustic stack may be incorporated within a PZT probe. The first matrix 200 is shown oriented along the azimuth direction 101 and the elevation direction 103.

Each of the elements 202 includes a first sub-element 204 and a second sub-element 206. As an example, the first sub-element 204 may be a higher frequency element and the second sub-element 206 may be a lower frequency element, where the first and second sub-elements 204, 206 may be coupled via a fabrication technique discussed further below, with reference to FIGS. 10-38. The elements 202 may be spaced apart from one another and thereby electrically insulated from adjacent elements 202. Each of the elements 202 may be coupled to an electrical circuit 208 to enable application of a voltage to induce deformation of each of the elements 202. Furthermore, each of the elements 202 may transmit an individual signal, as induced by deformation. It will be noted that each of the elements 202 are coupled to the electrical circuit 208 but only the bottom row of elements 202 are shown directly coupled to the electrical circuit 208 in FIG. 2 for brevity.

The first matrix 200 may be coupled to other layers of the acoustic stack, e.g., an acoustic lens, a backing, etc., as shown in FIG. 1. As a result of forming the elements from the first sub-element 204 and the second sub-element 206, the elements may transmit and/or receive across a wide range of frequencies. For example, the first sub-element 204 may have a central (e.g., resonance) frequency of 2.0 MHz and the second sub-element 206 may have a central frequency of 15 MHz. By combining the first sub-element 204 with the second sub-element 206 with equal relative proportions, the elements 202 may transmit and/or receive ultrasonic signals across a wider range of frequencies than either the first sub-element 204 or the second sub-element 206 alone.

For example, the each of the elements 202 may have a frequency range of 1.5 to 15 MHz. The array of the elements 202 in the first matrix 200 may provide symmetric and linear apodization functions along the elevation direction 103, as shown in FIG. 3. Apodization provided by both a high frequency sub-element (e.g., the first sub-element 204 of FIG. 2), as indicated by plot 302, and a low frequency sub-element (e.g., the second sub-element 206 of FIG. 2), as indicated by plot 304, are illustrated in graph 300. The apodization functions are plotted relative to percent content of the high frequency and low frequency sub-elements in each element of a transducer array along the y-axis and to the elevation direction 103 along the x-axis. The equal proportions of the high frequency sub-element and low frequency sub-element distributed along the elevation direction results in a uniform apodization function.

As described above, a symmetric and non-tapering apodization function may be provided by the high frequency and low frequency sub-elements 204, 206 of the elements 202 of FIG. 2 with equal proportions of the sub-elements in a homogeneous matrix array, e.g., each multi-frequency element of the array is configured similarly. However, in order to bring a sampled signal down to zero, or near zero, at edges of a sample region to suppress leakage sidelobes, a tapering of the apodization function may be desired. For example, a tapered apodization function (non-discretized) provided by an element formed of a high frequency sub-element and a low frequency sub-element is shown in a second graph 3900 in FIG. 39.

Plot 3902 represents an apodization function of the high frequency sub-element in each element of a transducer array relative to percent content (y-axis) along the elevation direction 103 and plot 3904 represents an apodization function of the low frequency sub-element in each element of the transducer array. Plot 3902 and plot 3904 are inversely correlated so that a maximum of the first plot 3902, relative to the y-axis, at a central region of the transducer array along the elevation direction 103 corresponds to a minimum of plot 3904. To either side of the maximum, plot 3902 decreases along the y-axis and the plot 3904 increases proportionally. While the maximum percent content of each of the high frequency and low frequency sub-elements is shown at 80% and the minimum percent content is shown at 20%, other examples may include any other values of the maximum and minimum percent content, such as 100% and 0%, respectively.

A sum of the high frequency and low frequency apodization functions may provide side lobe reduction. For example, it may be desirable to have a higher proportion of high frequency elements at a central region of the transducer array and higher proportion of the low frequency elements along the sides of the transducer array to achieve maximum suppression of leakage side lobes. The tapered apodization function shown in graph 3900 may be generated by configuring the elements of the transducer array with unequal relative proportions of each of the high and low frequency sub-elements. For example, a central region of the transducer may include elements with higher percent content of the high frequency sub-element than the outer edges. Suppression of side lobes is thereby enhanced.

Examples of elements with unequal sub-element proportions are shown in FIGS. 4-6. A first example of a multi-frequency element 400 with unequal distribution is shown in FIG. 4. The multi-frequency element 400 is formed of a first, high frequency sub-element 402 and a second, low frequency sub-element 404, similar to the first and second sub-elements 204, 206 of the elements 202 of FIG. 2.

A first width 406 of the first sub-element 402 may be greater than a second width 408 of the second sub-element 404. For example, the first width 406 may be four times greater than the second width 408, resulting in 80% of the multi-frequency element 400 formed of the first, high frequency sub-element 402 and 20% formed of the second, low frequency sub-element 404. The relative widths of the sub-elements may be reversed in other examples. A second example of a multi-frequency element 500 is shown in FIG. 5 and includes a first, high frequency sub-element 502 and a second, low frequency sub-element 504. In the second example, a first width 506 of the first sub-element 502 may be half of a second width 508 of the second sub-element 504.

In a third example of a multi-frequency element 600 with unequal distribution, as illustrated in FIG. 6, the multi-frequency element 600 is similarly formed of a first, high frequency sub-element 602 and a second, low frequency sub-element 604. A first width 606 of the first sub-element 602 is also less than a second width 608 of the second sub-element 604. The first width 606 may be, for example, a quarter of the second width 608.

The examples of multi-frequency elements with unequal distribution of sub-elements shown in FIGS. 4-6 are non-limiting examples of multi-frequency elements. Other examples, may include multi-frequency elements with any variation in relative proportions between the first sub-element and the second sub-element of the elements. Furthermore, other examples of the multi-frequency elements may include more than two sub-elements. For example, the multi-frequency elements may be formed of three or four sub-elements, with a variety of proportions of each of the sub-elements.

An array of non-homogeneous multi-frequency elements may be configured to provide the frequency apodization function shown in FIG. 39. The array may be non-homogeneous with respect to a percent content of different sub-elements forming each multi-frequency element included in the array. In other words, a number of sub-elements, each of the sub-elements having a different resonance frequency, as well as relative proportions of the sub-elements in each element may not be uniform across the array, enabling a spatial distribution of elements with different frequency ranges. In one example, as shown in FIG. 7, a second matrix 700, configured to provide an apodization function similar to that shown in graph 3900 of FIG. 39, may be an example of a one-dimensional (1D) linear array formed of a plurality of elements 702. A first row 701, a second row 703, and third row 705 of the plurality of elements 702 are depicted. Dotted lines between the second row 703 and the third row 705 represent a presence of optional additional rows arranged between the second row 703 and the third row 705, omitted from FIG. 7 for brevity. In other words, the second matrix 700 may have at least one row and may include any number of additional rows. Each of the plurality of elements 702 may be coupled to an electrical circuit and transmit an individual signal based on a composition of each element.

Each of the plurality of elements 702 includes a first, high-frequency sub-element 704 and/or a second, low-frequency sub-element 706. Some of the plurality of elements 702 include both the first sub-element 704 and the second sub-element 706 with varying widths of the sub-elements relative to one another (where the width is defined along the elevation direction 103). As well, some of the plurality of elements 702 include only the first sub-element 704 or only the second sub-element 706.

For example, a central region 720 of the second matrix 700 includes a portion of the plurality of elements 702 formed of only the first sub-element 704 while edge regions 722, distal to a central axis 708 of the second matrix 700, are formed of only the second sub-element 706. Regions 724 of the second matrix 700 between the central region 720 and the edge regions 722 are formed of both the first sub-element 704 and the second sub-elements 706 in varying ratios. As a result of a spatial distribution of the first and second sub-elements 704, 706 along the elevation direction 103, a resonance frequency of each of the plurality of elements 702 may vary along the elevation direction 103.

For example, in the central region 720 of the second matrix 700, the portion of the plurality of elements 702 that include only the first sub-element 704 may each transmit (and receive) signals at a resonance frequency associated with the first sub-element 704. At the edge regions 722, the portion of the plurality of elements 702 formed from only the second sub-element 706 may each transmit (and receive) signals at a resonance frequency associated with the second sub-element 706. In the regions 724 between the central region 720 and the edge regions 722, the plurality of elements 702 are hybrids, e.g., combinations of the first and second sub-elements 704, 706, and may therefore have a range of resonance frequency values in between those of the first and second sub-elements 704, 706.

As an example, a first element 707 of the plurality of elements 702 may be composed of 50% of the first sub-element 704 and 50% of the second sub-element 706. The resonance frequency of the first element 707 may be a value mid-way between that of the first sub-element 704 and the second sub-element 706. A second element 709 of the plurality of elements 702, positioned between the first element 707 and the central region 720 of the second matrix 700, may have a higher percent composition of the first sub-element 704 compared to the first element 707. The second element 709 may therefore have a resonance frequency that is higher than the first element 707 but lower than the resonance frequency of the first sub-element 704. A third element 711 of the plurality of elements 702, positioned between the first element 707 and the left-hand edge region 722 may have a higher percent composition of the second sub-element 706 than the first element 707. The third element 711 may there have a resonance frequency that is lower than the first element 707 but higher than the second sub-element 706.

By incrementally changing the composition of the plurality of elements 702 along the elevation direction 103, the plurality of elements 702 may have a continuum of resonance frequencies ranging between the resonance frequency of the first sub-element 704 and the resonance frequency of the second sub-element 706. In other examples, the composition of the plurality of elements 702 may be similarly varied along the azimuth direction 101 instead of the elevation direction 103 or in addition to the elevation direction 103. Thus the second matrix 700 may transmit and receive signals through a wider range of frequencies than a transducer array with a uniform element composition. In the example shown in FIG. 7, highest frequencies may be transmitted and received at the central region 720 of the second matrix while lowest frequencies may be transmitted and received at the edge regions 722.

The second matrix 700 may be symmetric about the central axis 708 of the second matrix 700, the central axis parallel with the azimuth direction 101. The symmetry of the second matrix 700, regardless of variations in distribution of the sub-elements amongst the plurality of elements 702, allows the second matrix to provide the apodization function as shown in FIG. 39.

An example of a third matrix 800 is illustrated in FIG. 8, which may be an example of a 1.5-dimensional (1.5D) matrix array. The third matrix 800 includes a plurality of elements 802 arranged in a first row 804, a second row 806, and a third row 808. Similarly, dotted lines between the first row 804 and the second row 806 indicate a presence of additional rows of the third matrix 800, omitted for brevity. The third matrix 800 has a central axis 810 parallel with the azimuth direction 101.

At least a portion of the plurality of elements 802 of the third matrix 800 may be multi-frequency elements 816 formed of a first, high-frequency sub-element 812 and a second, low-frequency sub-element 814. For example, the multi-frequency elements 816 of the plurality of elements 802 may include two of the first sub-element 812 alternating with two of the second sub-element 814 along the elevation direction 103. A central region 820 of the third matrix 800 may be formed only of the first sub-element 812 while edge regions 822 of the third matrix 800 may be formed of only the second sub-element 814. Furthermore, a thickness of each of the plurality of elements 802, defined along the elevation direction 103, may vary across each row of the third matrix 800.

As a result of a spatial distribution of the first and second sub-elements 812, 814 along the elevation direction 103, a resonance frequency of the plurality of elements 802 may vary across the elevation direction 103. For example, similar to the second matrix 700 of FIG. 7, a portion of the plurality of elements 802 in the central region 820 may transmit and receive signals at a higher resonance frequency equal to a resonance frequency of the first sub-element 812, while a portion of the plurality of elements 802 at the edge regions may transmit and receive signals at a lower resonance frequency equal to a resonance frequency of the second sub-element 814. A portion of the plurality of elements 802 between the central region 820 and the edge regions 822 may have intermediate resonance frequencies between those of the first sub-element 812 and the second sub-element 814. Thus a range of frequencies encompassed by the third matrix 800 may be broadened in comparison to use of a single frequency element in the array of the third matrix 800.

The third matrix 800 may be symmetric across the central axis 810, along the elevation direction 103. Similar to the second matrix 700 of FIG. 7, the symmetry of the third matrix 800 enables the third matrix 800 to provide the apodization function as shown in FIG. 39. The 1.5D array (as well as a 1.75D array) may provide an optimized beam pattern as an active aperture of a transducer probe changes. As such, the array is able to optimize a near field with a narrow aperture as well as a far field with a larger aperture. By manufacturing the 1.5D or 1.75D array via a process shown in FIGS. 10-38, the process allows mixing of elements with different central frequencies and frequency ranges within a single array. The manufacturing process provides increased flexibility in array configuration with incurring extensive additional costs. An example of a fourth matrix 900, which may be an example of a 1.25 linear array, is shown in FIG. 9. The fourth matrix 900 also has a plurality of elements 902, arranged in rows along the elevation direction 103, and a central axis 904, parallel with the azimuth direction 101. The plurality of elements 902 may each be formed of a single type of element and are not hybrid elements.

The fourth matrix 900 includes a first, high-frequency sub-element 906 and a second, low-frequency sub-element 908. Each of the plurality of elements 902 may be formed of either the first sub-element 906 or the second sub-element 908 and may vary in width along the elevation direction 103. A symmetry of the fourth matrix 900 across the central axis 904 along the elevation direction 103 also allows the fourth matrix 900 to provide apodization along the elevation direction 103. Incorporation of more than one type of element allows the fourth matrix 900 to operate across a wider range of frequencies. However, the frequency distribution may be less continuous and more discretized than the matrices of FIGS. 7 and 8 without incorporation of hybrid elements, e.g., elements formed of more than one sub-element.

It will be noted that each element of the plurality of elements of FIGS. 7-9 may be coupled to an electrical circuit, as shown in FIGS. 1 and 2. Additionally, other examples of a multi-frequency transducer array may also include control of frequency apodization and agility along the azimuth direction 101. For example, a distribution of multi-frequency elements may be varied along the azimuth direction 101 in a similar manner as shown along the elevation direction 103. Varying a spatial frequency distribution along the azimuth direction may be implemented in an array as an alternative or in addition to frequency variation along the elevation direction. By configuring the array with multi-frequency elements along both the azimuth and elevation directions, more complex apodization is enabled relative to frequency apodization in a transducer array with uniform elements. By providing a method to vary the elements along both directions, a configuration of the array is more flexible and may be implemented more easily as a matrix. Furthermore, the frequency agility, e.g., an ability of a transducer to quickly shift a transmitted frequency over a pre-selected range to mitigate jamming, mutual interference or account for atmospheric effects, may be enabled along both the azimuth and elevation directions.

Incorporation of multi-frequency elements into a transducer array may enable enhanced sensitivity for both transmission and reception of signals while increasing a frequency bandwidth of the transducer array. Signal transmission at a specific frequency, based on an application of a transducer probe, may be selected, resulting in energization of multi-frequency elements in the transducer array with a corresponding resonance frequency. By configuring the transducer array with elements with a broad range of frequencies, different operation of the transducer probe is enabled. The transducer probe may thereby be used for a variety of applications that would otherwise demand use of multiple single element transducer probes with different resonance frequencies.

In some examples, post-processing of signals received by the transducer array may be similar to conventional post-processing, utilizing already existing post-processing algorithms to convert the signals into, for example, images. Bandpass filtering of the signals may be modified based on the frequency of the signal.

Fabrication of an array of multi-frequency transducer elements may be achieved via a cost-effective process leveraging a wafer level approach. The wafer level approach allows multiple transducer arrays to be generated simultaneously, thereby increasing efficiency and throughput. A fabrication process for a multi-frequency transducer array is now described with reference to FIGS. 10-38 and 40-42. The wafer level approach may begin with a block of a first acoustic stack 1000, as shown in FIG. 10. The first acoustic stack 1000 is viewed along the elevation direction in FIG. 10 and includes a matching layer 1002, similar to the acoustic matching layer 120 of FIG. 1, which may be an electrically conductive layer such as graphite or a metal. The matching layer 1002 may be formed of more than one layer stacked along a vertical axis of the first acoustic stack 1000, e.g., along the transverse direction 105, configured to be electrically conductive along the vertical axis.

The matching layer 1002 is arranged above, relative to the transverse direction 105, a first piezoelectric layer 1004. An acoustic impedance difference between an ultrasound transducer probe and a target medium may be buffered by the matching layer 1002. The first piezoelectric layer 1004 is formed of a piezoelectric material configured to transmit and/or receive ultrasound signals and used to form transducer elements of an ultrasound transducer probe, as described above.

A dematching layer 1006 may be positioned below the first piezoelectric layer 1004. The dematching layer may be a high impedance layer that may decrease insertion losses and enhance a frequency bandwidth of a transducer probe. In some examples, the dematching layer may be optionally omitted. A backing layer 1008, similarly to the backing 126 of FIG. 1, may be arranged below the dematching layer 1006. The backing layer 1008 may be formed of an electrically conductive material, such as a composite, for example, and may dampen a ringing effect which may occur when the piezoelectric material switches from a transmission mode to a receiving mode. The first piezoelectric layer 1004 may be bonded to the matching layer 1002 and to the dematching layer 1006 (or to the backing layer 1008 when the dematching layer 1006 is not present) with an adhesive such as epoxy.

The first piezoelectric layer 1004 of the first acoustic stack 1000 may have a first height 1010, defined along the transverse direction 105. The first height 1010 may visually differentiate a piezoelectric element with a higher resonance frequency from a resonance frequency piezoelectric element of a second piezoelectric layer 1204 with a larger second height 1210, shown in FIGS. 12 and 13 and described further below. A first comb structure 1100 may be produced from the first acoustic stack 1000 of FIG. 10 by dicing kerfs 1102 evenly spaced along the transverse direction 105 on the first acoustic stack 1000. The kerfs 1102 extend downwards, along the azimuth direction 101, from the matching layer 1002 into the backing layer 1008 but not entirely through the backing layer 1008. Dicing of the kerfs 1102 forms first fins 1104, each of the first fins 1104 spaced apart from adjacent first fins 1104 by one of the kerfs 1102. The first fins 1104 extend upwards along the azimuth direction 101 from the backing layer 1008 and may extend along the elevation direction 103 across an entire depth of the first comb structure 1100.

It will be noted that dicing refers to cutting of kerfs into a wafer to form cavities or slots in the wafer that do not extend entirely through a height of the wafer. Thus dicing may electrically isolate portions of the wafer, e.g., renders a section electrically discontinuous from an adjacent section along a plane perpendicular to the height, but does not divide the wafer into individual, separate sections. In contrast, singulation facilitates singularizing of the wafer into individual transducer arrays that are physically separated, as described below. Herein, dicing and singulation are conducted only along the height of the wafer, e.g., along the transverse direction so that portions of the wafer are electrically isolated and/or physical separated only along the plane formed by the azimuth and the elevation directions.

Figure 13:
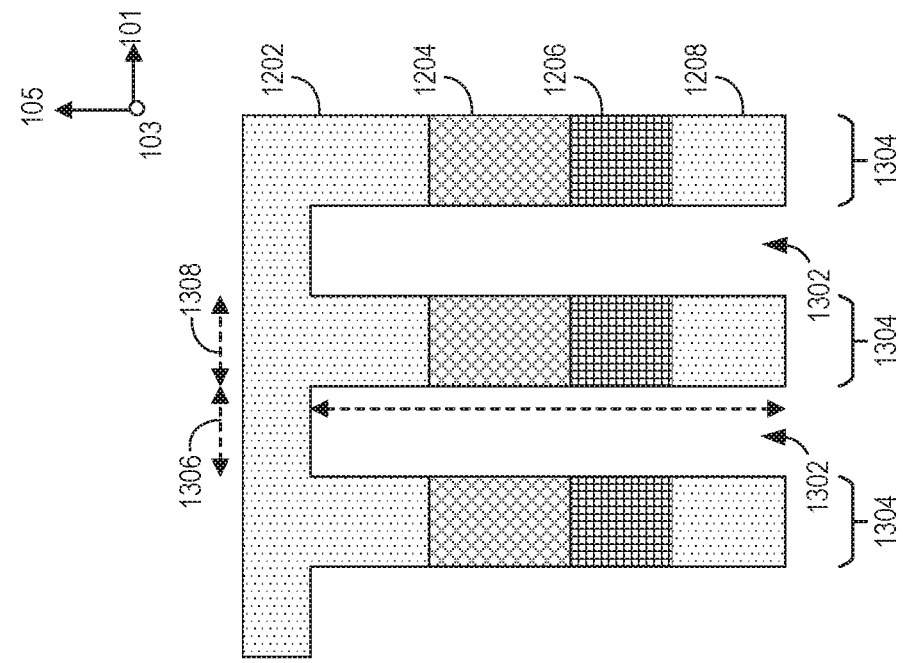
FIG. 13 shows a second comb structure formed from the acoustic stack of FIG. 12.
Figure 12:
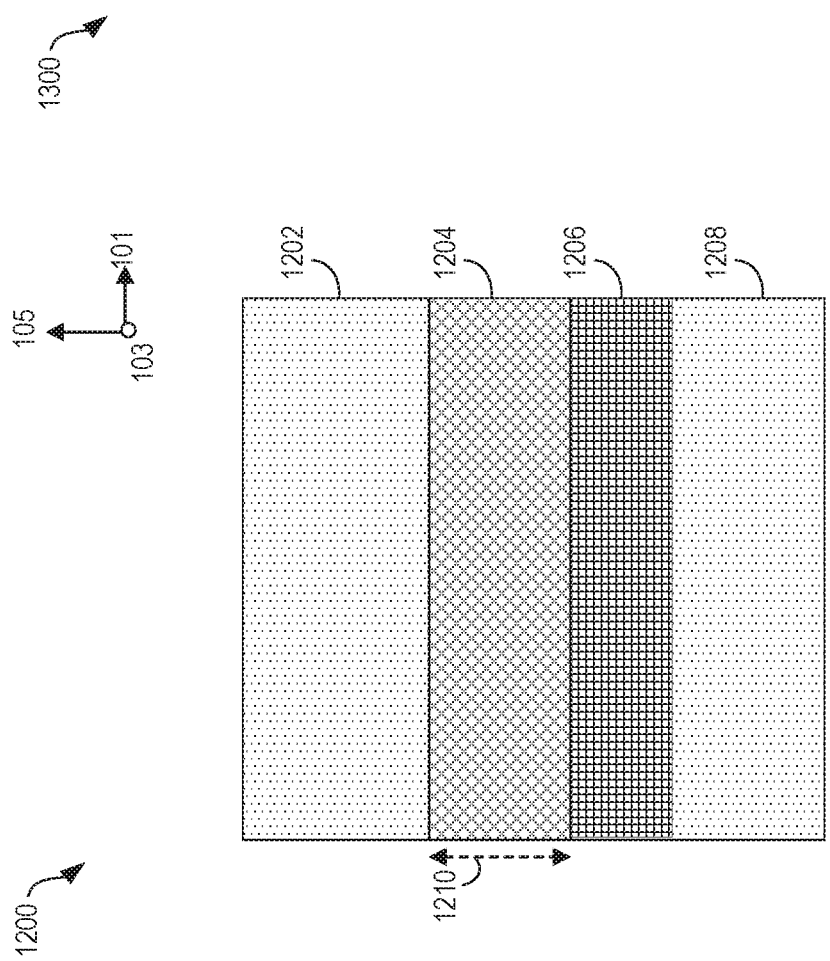
FIG. 12 shows a second example of an acoustic stack block.

The first comb structure 1100 may be diced into a geometry to complement or match a second comb structure (e.g., a second comb structure 1300 shown in FIG. 13. The second comb structure 1300 may be formed from a second acoustic stack 1200, depicted in FIG. 12. The second acoustic stack 1200 may have similar layers to the first acoustic stack 1000, including a matching layer 1202, formed of a same or different material (or stack of electrically conductive layers) as the matching layer 1002 of the first acoustic stack 1000, a second piezoelectric layer 1204, formed of a different material as the first piezoelectric layer 1004 of FIG. 10, an optional dematching layer 1206, similar to the dematching layer 1006 of the first acoustic stack 1000, and a backing layer 1208, formed of a same or different material as the backing layer 1008 of the first acoustic stack 1000.

As described above, the second height 1210, defined along the azimuth direction 101, of the second piezoelectric layer 1204 may be greater than the height 1010 of the first piezoelectric layer 1004 of the first acoustic stack 1000. Piezoelectric elements formed from the second piezoelectric layer 1204 may have a lower resonance frequency than the piezoelectric elements formed from the first piezoelectric layer 1004. The diced piezoelectric elements corresponding to the first piezoelectric layer 1004, e.g., in the first comb structure 1100, are hereafter referred to as high frequency sub-elements 1004 and the diced piezoelectric elements corresponding to the second piezoelectric layer 1204, e.g., in the second comb structure 1300, are hereafter referred to as low frequency sub-elements 1204.

A height, also defined along the azimuth direction 101, of the matching layer 1202 of the second acoustic stack 1200 may be greater than a height of the matching layer 1002 of the first acoustic stack 1000 while a height of the backing layer 1208 of the second acoustic stack 1200 may be less than a height of the backing layer 1008 of the first acoustic stack 1000. The difference in heights between the matching layers and the backing layers may allow the layers of each of the first and second comb structures 1100, 1300 to have a desired alignment when the comb structures are combined into a single structure, described further below.

The second acoustic stack 1200 may be diced in an opposite direction from the first acoustic stack 1000, as shown in FIG. 13. As such, the second acoustic stack 1200 is diced so that kerfs 1302 extend from the backing layer 1208 upwards, along the azimuth direction 101, into the matching layer 1202. The kerfs 1302 do not extend entirely through the matching layer 1202. The kerfs 1302 are evenly spaced apart along the transverse direction 105, forming second fins 1304 between each of the kerfs 1302. The second fins 1304 may extend across an entire depth of the second comb structure 1300 along the elevation direction 103.

A width 1306 of each of the kerfs 1302 of the second comb structure 1300 may be equal to a width 1106 (as shown in FIG. 11) of each of the first fins 1104 of the first comb structure 1100. Similarly, a width 1308 of each of the second fins of the second comb structure 1300 may be equal to a width 1108 (as shown in FIG. 11) of each of the kerfs 1102 of the first comb structure 1100. A height 1310, defined along the azimuth direction 101, of both the kerfs 1302 of the second comb structure 1300 and the second fins 1304 may equal a height of both the first fins 1104 and the kerfs 1102 of the first comb structure 1100. The complementary geometries of the first comb structure 1100 and the second comb structure 1300 allow the comb structures to fit together to form a third acoustic stack 1402 with interdigitated comb structures, as shown in FIG. 14 from a first view 1400 along the elevation direction 103 and in FIG. 15 from a second view 1500 along the azimuth direction 101.

Figure 14:
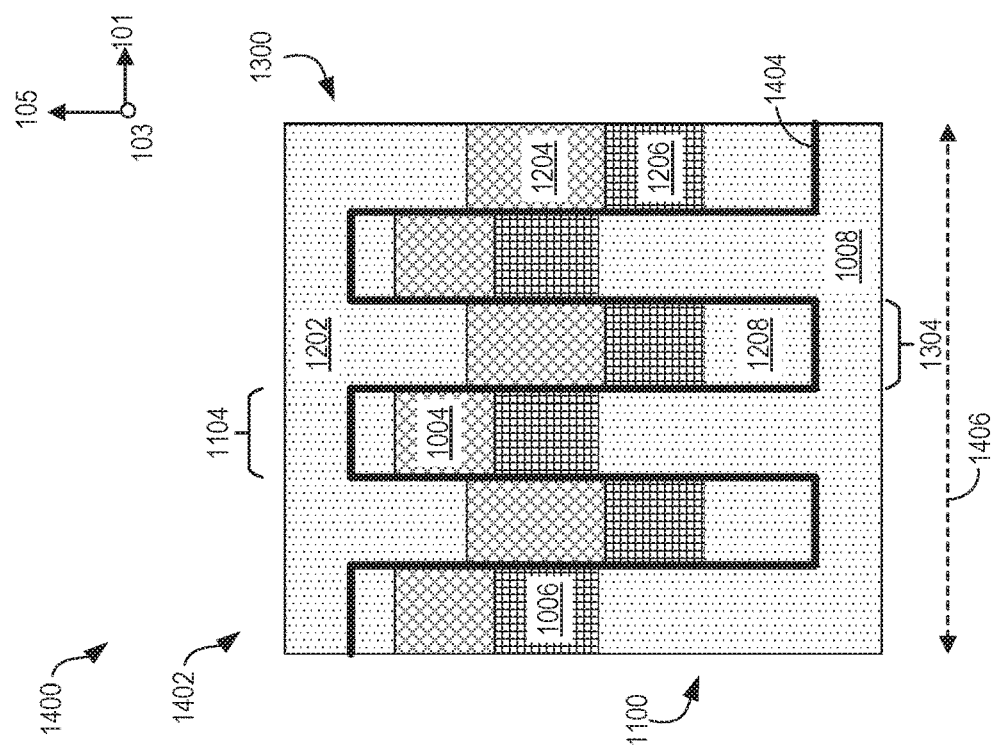
FIG. 14 shows a third example of an acoustic stack block, formed by coupling the first example of FIG. 10 with the second example of FIG. 12, from a view along the elevation direction.

In the first view 1400 of the third acoustic stack 1402, illustrated in FIG. 14, a first layer of adhesive 1404 is arranged between the first comb structure 1100 and the second comb structure 1300 to enable lamination of the comb structures. The first layer of adhesive 1404 may be a non-conductive glue, such as epoxy, that electrically insulates the first comb structure 1100 from the second comb structure 1300. The first comb structure 1100 and the second comb structure 1300 may be nested into one another so that there are no gaps between the first comb structure 1100 and the second comb structure 1300.

As shown in the second view 1500 of the third acoustic stack 1402, the first fins 1104 and the second fins 1304, each fin forming a digit of the interdigitated structure of the third acoustic stack 1402, extends along a depth 1502 of the third acoustic stack 1402 along the elevation direction 103. It will be appreciated that the first view 1400 and the second view 1500 of the third acoustic stack 1402 may represent a section of the third acoustic stack rather than the entire acoustic stack 1402. While the third acoustic stack 1402 is shown with three of the first fins 1104 and three of the second fins 1304 in FIG. 14, the third acoustic stack 1402 may have any number of the fins. The third acoustic stack 1402 may have a width 1406 and depth 1502 greater or less than shown in FIGS. 14 and 15, respectively.

Additionally, in some examples, the third acoustic stack 1402 may be further combined with one or more additional comb structures to increase a number of sub-elements with different resonance frequencies incorporated into an acoustic stack. For example, as shown in FIG. 36, a first multi-frequency comb structure 3602 and a second multi-frequency comb structure 3604 may each be formed from an acoustic stack such as the third acoustic stack 1402.

At least one first fin 3603 of the first multi-frequency comb structure 3602 may include a first sub-element 3606 and a second sub-element 3608. The first multi-frequency comb structure 3602 may be formed by dicing an acoustic stack similarly to the dicing of the first acoustic stack 1000 as shown in FIG. 11, with a first kerf 3610 extending downwards from a top of the first multi-frequency comb structure 3602, along the transverse direction 105, through a portion of a height 3612 of the first multi-frequency comb structure 3602.

The second multi-frequency comb structure 3604 may have at least one second fin 3614, the second fin 2614 including a third sub-element 3616 and a fourth sub-element 3618. Each of the first, second, third, and fourth sub-elements 3606, 3608, 3616, 3618 may have different resonance frequencies. The second multi-frequency comb structure 3604 may be diced similarly to the second acoustic stack 1200 as shown in FIG. 13, with a second kerf 3620 extending upwards from a bottom of the second multi-frequency comb structure 3604, along the transverse direction 105, through a portion of a height 3622 of the second multi-frequency comb structure 3604.

A width 3624 and a height 3626 of the first kerf 3610 may be similar to a width and a height of the second fin 3614. A width 3628 and a height 3630 of the second kerf 3620 may be similar to a width and a height of the first fin 3603. The second fin 3614 of the second multi-frequency comb structure 3604 may be inserted into the first kerf 3610 of the first multi-frequency comb structure 3602 while the first fin 3603 may be inserted into the second kerf 3620 of the second multi-frequency comb structure 3604, as indicated by arrows 3632 to form a combined stack with four sub-elements. The combined stack may be laminated and further processed as described below.

FIG. 36 shows a non-limiting example of how a multi-frequency acoustic stack with four different sub-elements may be formed. In other examples, either of the first multi-frequency comb structure 3602 or the second multi-frequency comb structure 3604 may be a single element comb structure. In such instances, a resulting combined acoustic stack may include three sub-elements. Furthermore, widths, defined along the azimuth direction 101, of each of the sub-elements are shown to be similar, resulting in a combined stack with equal proportions of each sub-elements. In other examples, however, the widths of the sub-elements may be varied so that the percent content of each of the sub-elements is not equal.

Figure 15:
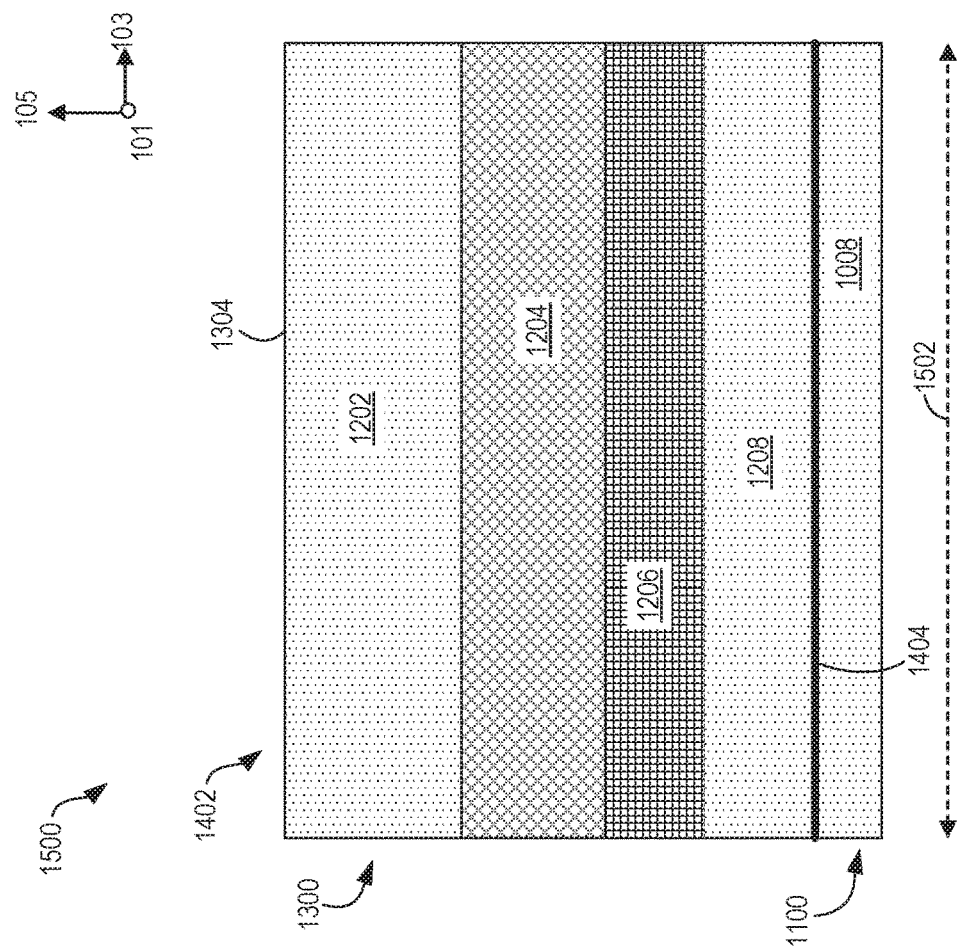
FIG. 15 shows the third example of the acoustic stack block from a view along the azimuth direction.

Furthermore, while the third acoustic stack 1402 of FIGS. 14-15 show the first and second comb structures 1100, 1300 having complementary geometries that result in a gap-free combining of the comb structure, e.g., no spaces are present between the comb structures when coupled, the comb structures may be diced to have non-matching geometries. For example, as shown in FIG. 42, an alternate example of an acoustic stack 4200 may include a first comb structure 4202 and a second comb structure 4204, combined to form an interdigitated structure.

Kerfs of the first comb structure 4202 may not have dimensions that match dimensions of fins of the second comb structure 4204 and kerfs of the second comb structure 4204 may not have dimensions matching fins of the first comb structure 4202. For example a first kerf 4206 of the first comb structure 4202 may have a depth 4208 that is greater than a depth 4210 of a first fin 4212 of the second comb structure 4204. When the first fin 4212 of the second comb structure 4204 is inserted into the first kerf 4206 of the first comb structure 4204, gaps may be present around the first fin 4212, e.g., along the azimuth direction.

A second kerf 4214 of the first comb structure 4202 may also have a depth 4216 that is greater than a depth 4218 of a second fin 4220 of the second comb structure 4204. When the second fin 4220 of the second comb structure 4204 is inserted into the second kerf 4214 of the first comb structure 4202, gaps may be present around the second fin 4220, e.g., along the azimuth direction 101. The gaps around the second fin 4220 may be greater than the gaps around the first fin 4212 due to either non-uniform depths of the kerfs of the first comb structure 4204 and/or non-uniform depths of the fins of the second comb structure 4204. The fins of the first comb structure 4202 may be similarly surrounded by gaps due to greater depths of the kerfs of the second comb structure 4204 compared to depths of the fins of the first comb structure 4204.

Figure 42:
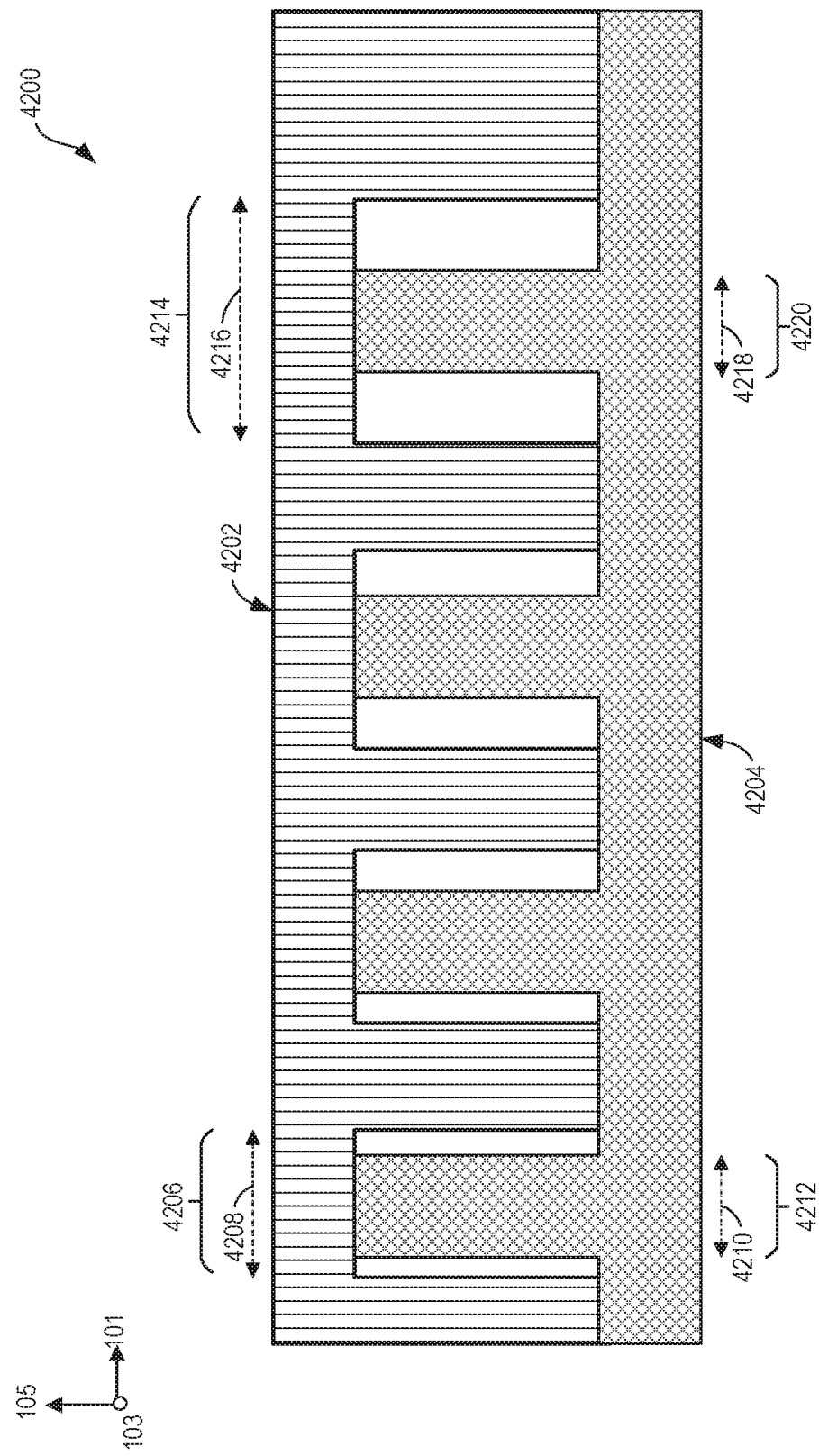
FIG. 42 shows an example of an acoustic stack formed from comb structures with different kerf dimensions.

As shown in FIG. 42, a variety of geometries of the acoustic stack, formed by combining at least two comb structures, may be enabled by adjusting dimensions of the kerfs and fins. The dicing and combining of the comb structures introduces a high degree of flexibility in a final configuration of a transducer array. Thus modification of the transducer may be efficiently modified.

Figure 16:
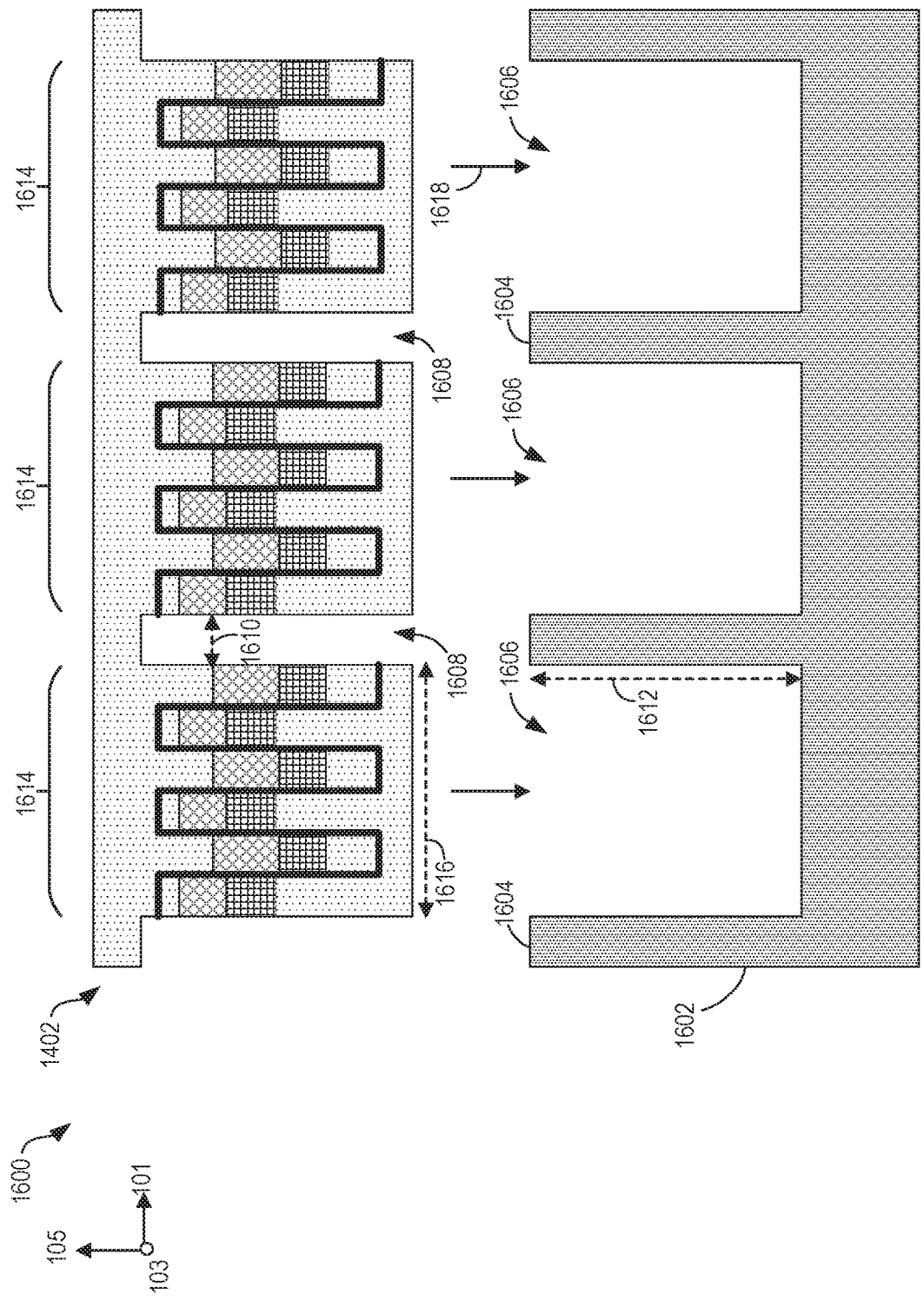
FIG. 16 shows a coupling of the third example of the acoustic stack block with a base package from a view along the elevation direction.
Figure 17:
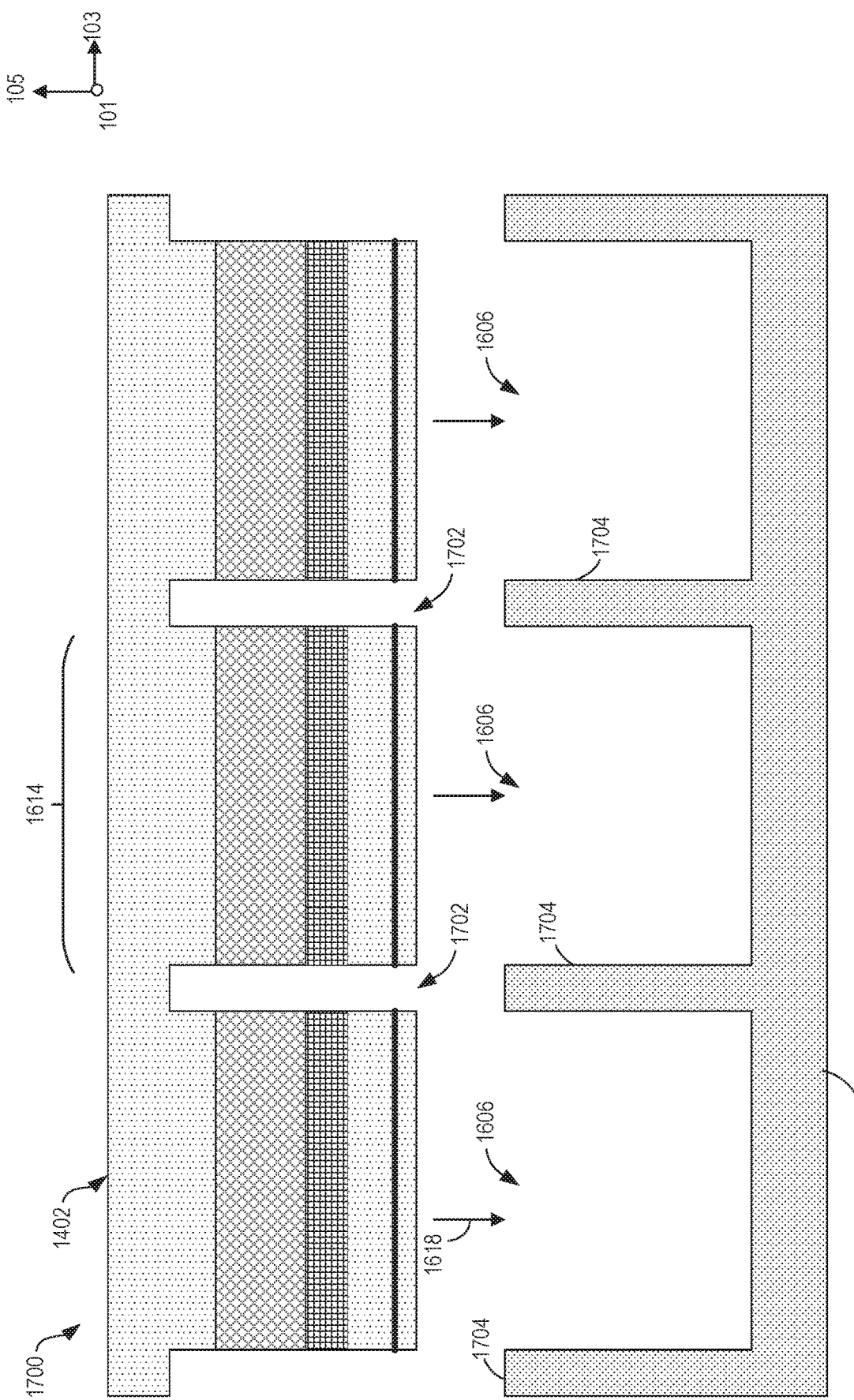
FIG. 17 shows the coupling of third example of the acoustic stack block with the base package from a view along the azimuth direction

Turning now to FIGS. 16-17, the third acoustic stack 1402 may be combined with a first example of a base package 1602, as shown in a first view 1600 along the elevation direction 103 in FIG. 16 and in a second view 1700 along the azimuth direction 101 in FIG. 17. The base package 1602 may be formed from a conductive material such as graphite, porous graphite filled with resin, stainless steel, aluminum etc. The base package 1602 may be diced to have first fins 1604, extending along the transverse direction 105, and kerfs 1606. The third acoustic stack 1402 may also be diced to have first kerfs 1608, also extending along the elevation direction 103, that match the first fins 1604 of the base package 1602 in a width 1610 and a height 1612. Dicing of the third acoustic stack 1402 also forms blocks 1614 with the same height 1612 as the first fins 1604 of the base package 1602 and with a width 1616 of each of the blocks 1614 equal to a width of the kerfs 1606 of the base package 1602.

The dicing of the third acoustic stack 1402 and the base package 1602 are further shown in FIG. 17. The third acoustic stack 1402 may have second kerfs 1702, extending along the azimuth direction 101, in addition to the kerfs 1606. The base package 1602 has second fins 1704 which may be continuous with the first fins 1604 but extending along a perpendicular direction from the first fins 1604, e.g., along the azimuth direction 101. As such, the first fins 1604 and the second fins 1704 may form a structure as shown in a perspective view 1800 in FIG. 18.

The base package 1602 is depicted in the perspective view 1800 to show an overall geometry of the first fins 1604, the second fins 1704 and the kerfs 1606 of the base package 1602. The first fins 1604 and the second fins 1704 frame each of the kerfs 1606 so that each of the kerfs 1606 has a uniform rectangular geometry. In other examples, however, the kerfs 1606 may have a variety of other geometries, such as circular, hexagonal, square, etc. As such, transducers produced by the manufacturing process depicted in FIGS. 10-35 may have a shape corresponding to a geometry of the kerfs 1606.

The kerfs 1606 form cavities in the base package 1602 and the blocks 1614 of the third acoustic stack 1402 (as shown in FIGS. 16 and 17) are shaped to match the geometry of the kerfs 1606. In this way, the kerfs 1606 of the base package 1602 receive the blocks 1614 of the third acoustic stack 1402, as indicated by arrows 1618 in FIGS. 16 and 17, the first kerfs 1608 of the third acoustic stack 1402 receive the first fins 1604 of the base package 1602, and the second kerfs 1702 of the third acoustic stack 1402 receive the second fins 1704 of the base package 1602.

Figure 18:
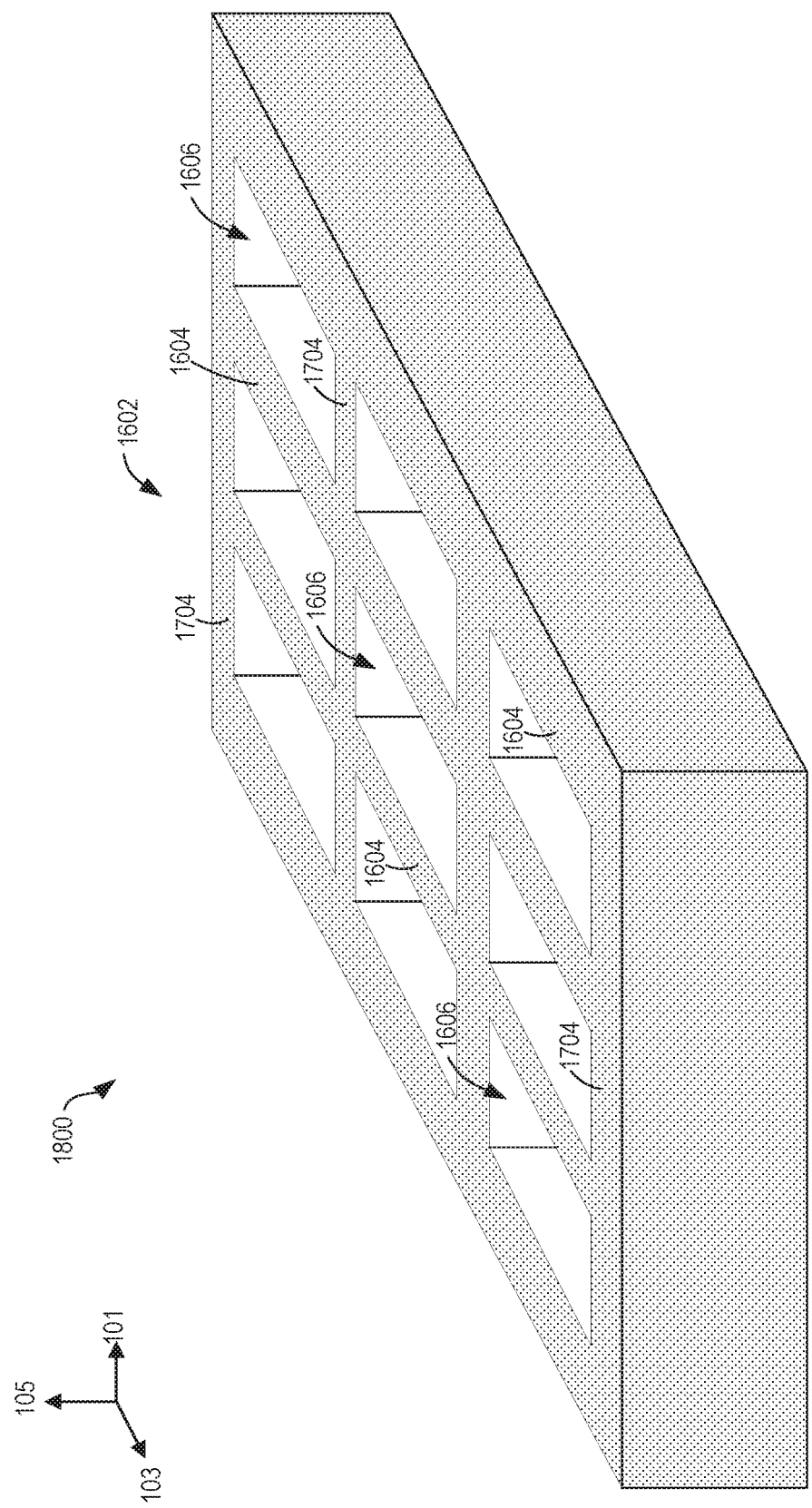
FIG. 18 shows a first example of a base package from a perspective view.
Figure 40:
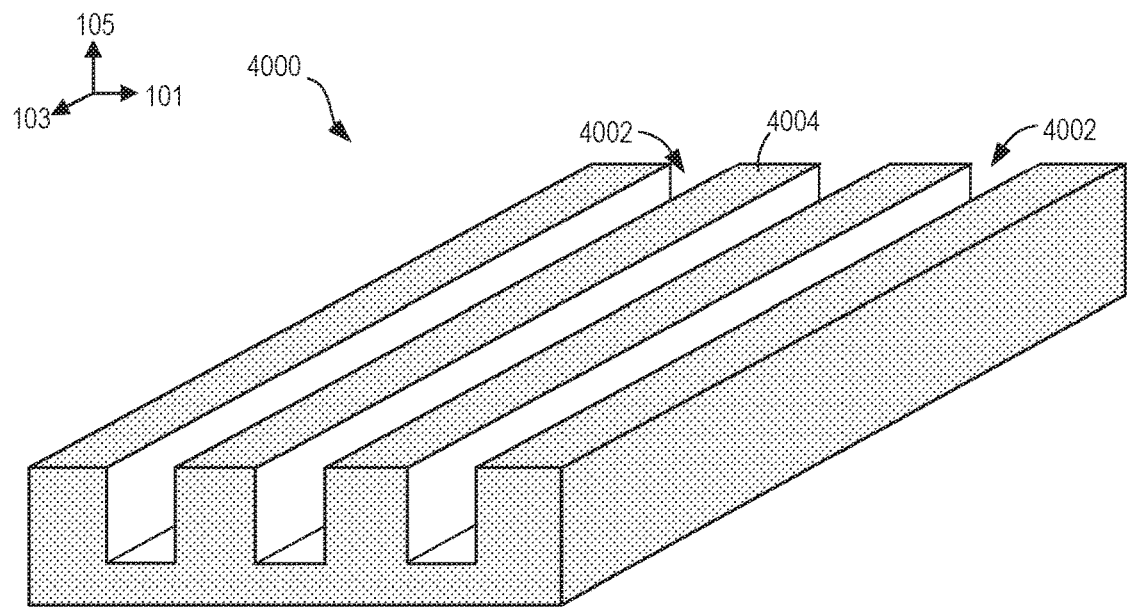
FIG. 40 shows a second example of a base package from a perspective view.

In other examples, a base package may be configured differently than the base package 1602 of FIG. 18. For example, as shown in FIG. 40, a second example of a base package 4000, may have kerfs 4002 extending linearly and continuously along the elevation direction 103. The kerfs 4002 are parallel and may extend across an entire depth of the base package 4000, the depth defined along the elevation direction 103, or across at least a portion of the depth. Fins 4004 of the base package 4000, spaced apart by the kerfs 4002, may also extend along the elevation direction 103. An acoustic stack may be similarly diced along the elevation direction 103 to match the kerfs 4002 and fins 4004 of the base package 4000.

Figure 41:
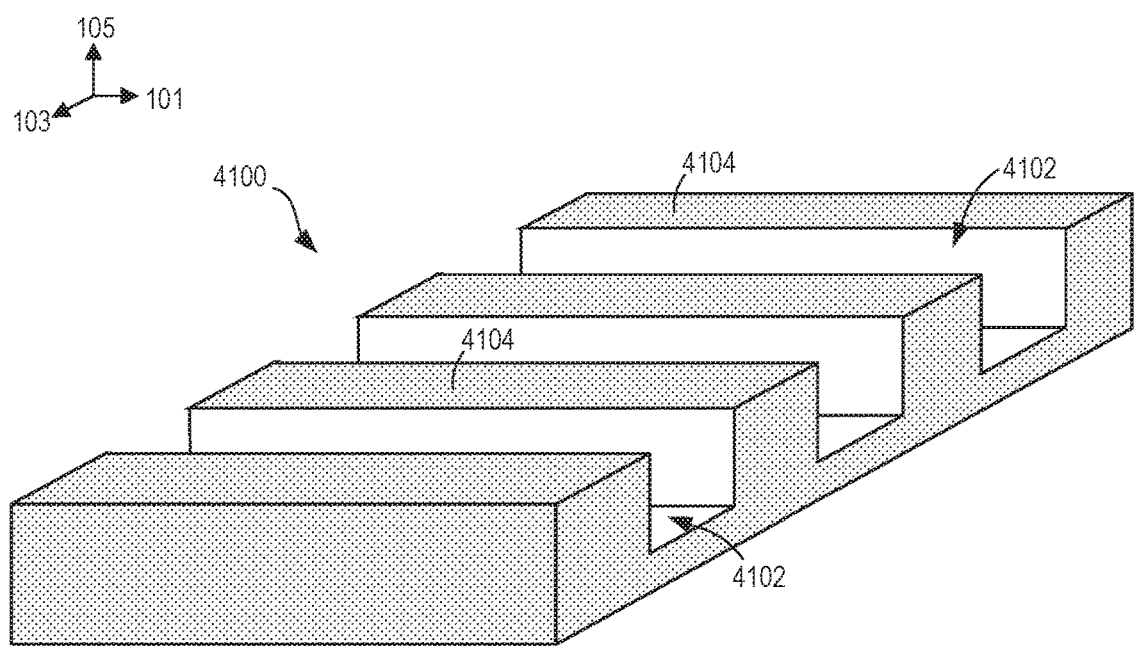
FIG. 41 shows a third example of a base package from a perspective view.

Alternatively, a base package may be diced entirely along the azimuth direction 101, as shown in FIG. 41. FIG. 41 depicts a third example of a base package 4100 with kerfs 4102 and fins 4104 extending along the azimuth direction 101. The kerfs 4102 and fins 4104 may extend entirely or partially across a width of the base package 4100, the width defined along the azimuth direction 101. An acoustic stack may be diced with kerfs and blocks to match a geometry of the base package 4100, e.g., with kerfs and blocks extending along the azimuth direction 101.

Figure 19:
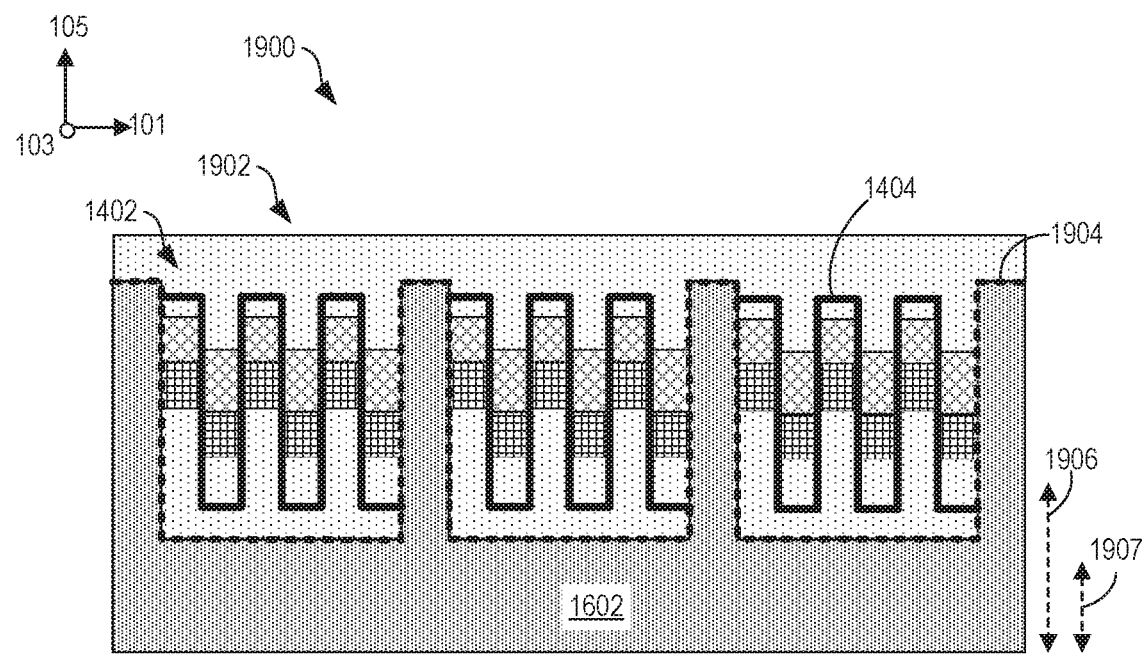
FIG. 19 shows a fourth example of an acoustic stack block, formed from the coupling of the third example of the acoustic stack block with the base package, viewed along the elevation direction.
Figure 20:
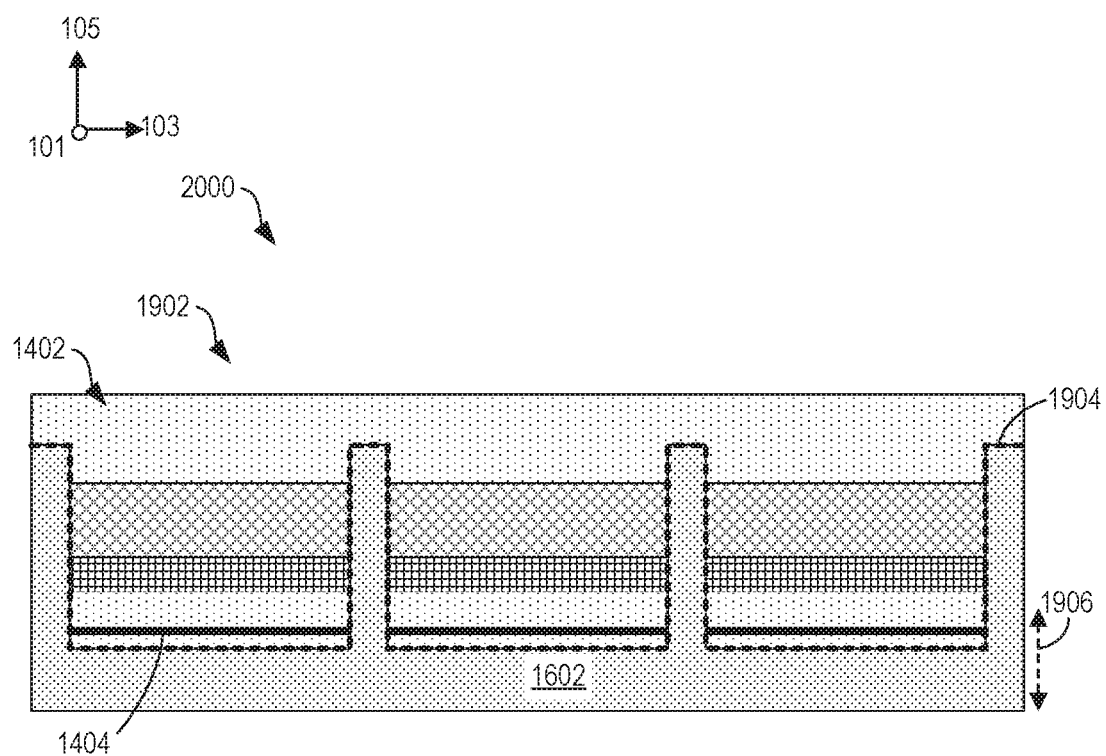
FIG. 20 shows the fourth example of an acoustic stack block viewed along the azimuth direction.

Turning now to a first view 1900 along the elevation direction in FIG. 19 and a second view 2000 along the azimuth direction 101 in FIG. 20, the third acoustic stack 1402 and the base package 1602 may be laminated with a second layer of adhesive 1904, disposed between the third acoustic stack 1402 and the base package 1602, to form a fourth acoustic stack 1902. The second layer of adhesive 1904 is illustrated as a dotted line to differentiate the second layer of adhesive 1904 from the first layer of adhesive 1404. The second layer of adhesive 1904 may also be a non-conductive glue that electrically isolates the third acoustic stack 1402 from the base package 1602.

Figure 21:
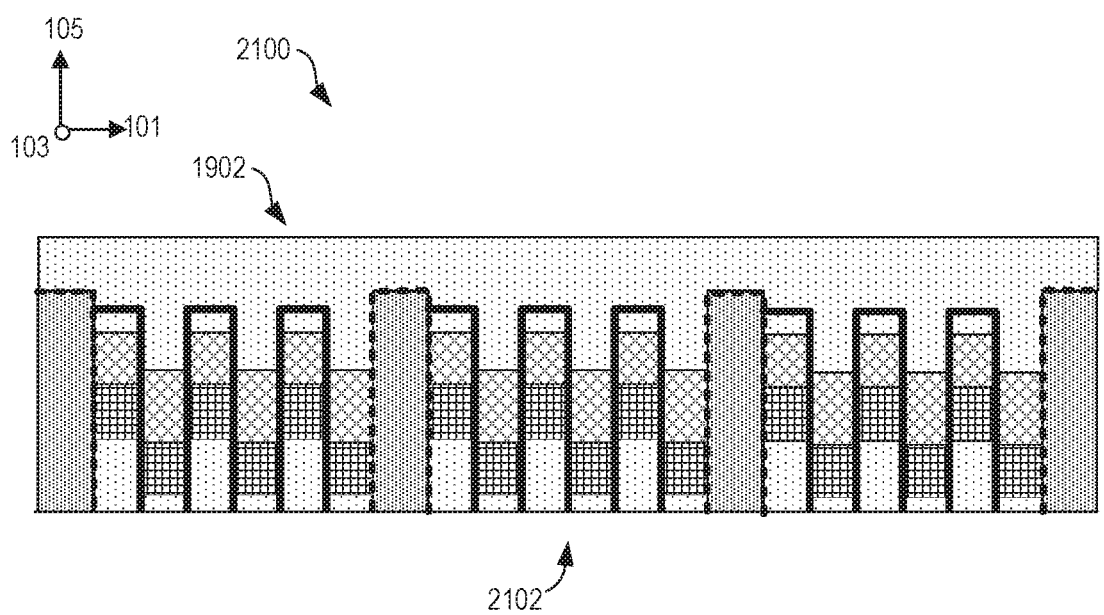
FIG. 21 shows the fourth example of the acoustic stack block of FIG. 19 with a portion of a back side of the acoustic stack block ground away, viewed along the elevation direction.
Figure 22:
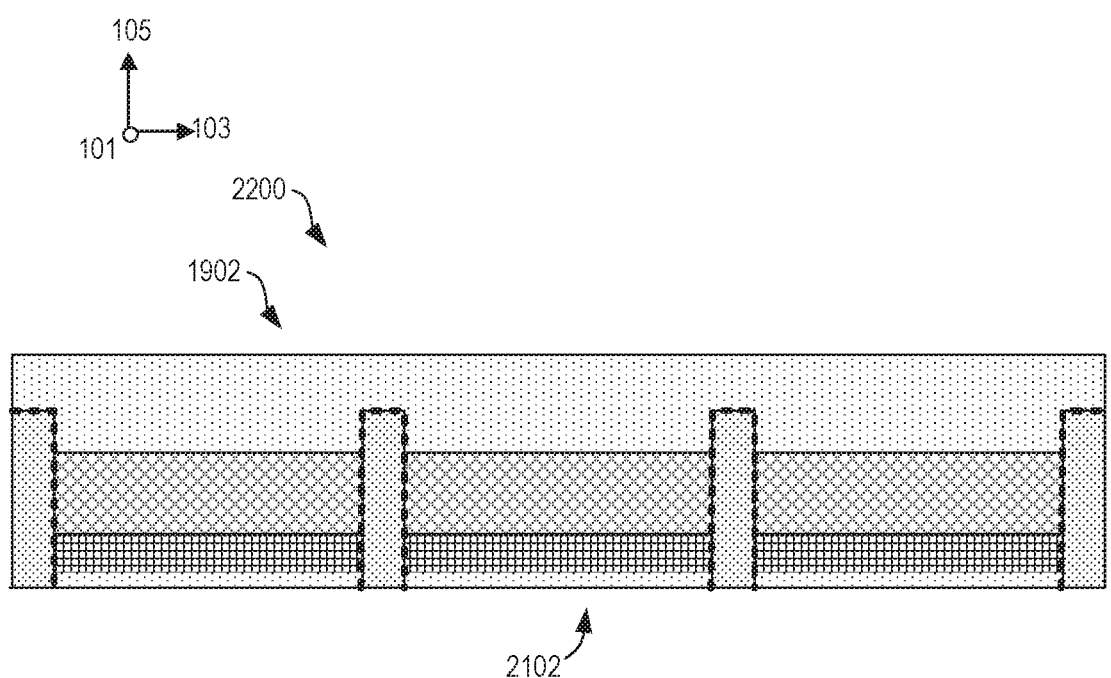
FIG. 22 shows the fourth example of the acoustic stack block of FIG. 20 with the portion of the back side of the acoustic stack block ground away, viewed along the azimuth direction.

As shown in a first view 2100 of the fourth acoustic stack 1902 along the elevation direction 103 in FIG. 21 and in a second view 2200 of the fourth acoustic stack 1902 along the azimuth direction in FIG. 22, a back side 2102 of the fourth acoustic stack 1902 may be subjected to grinding. Ground recovery in both the elevation direction 103 and the azimuth direction 101 is enabled by grinding the back side 2102 so that a portion of the base package 1602, a portion of the backing layer 1008 of the first comb structure 1100, and a portion of the backing layer 1208 of the second comb structure 1300 (the backing layers 1008, 1208 shown in FIGS. 14-15) is removed. The back side 2102 of the fourth acoustic stack may provide a positive terminal connectivity. A height 1906 of an overall portion of the fourth acoustic stack 1902 that is ground away is shown in FIGS. 19 and 20.

The back side 2102 of the fourth acoustic stack 1902 is ground until portions of both the first layer of adhesive 1404 and the second layer of adhesive 1904 that are parallel with the elevation direction 103 (as shown in FIGS. 19 and 20) are removed. By removing the portions of the adhesive layers, e.g., bottom portions of the adhesive layers relative to the azimuth direction 101, ground recovery in both the elevation and azimuth directions is enabled. In other words, electrical continuity between the elements (e.g., the high frequency sub-elements 1004 and the low frequency sub-elements 1204) and electrical contacts or electrodes (not shown in FIGS. 21 and 22), arranged in contact with the back side 2102 of the fourth acoustic stack 1902, is provided by removing the insulating adhesive layers.

Figure 23:
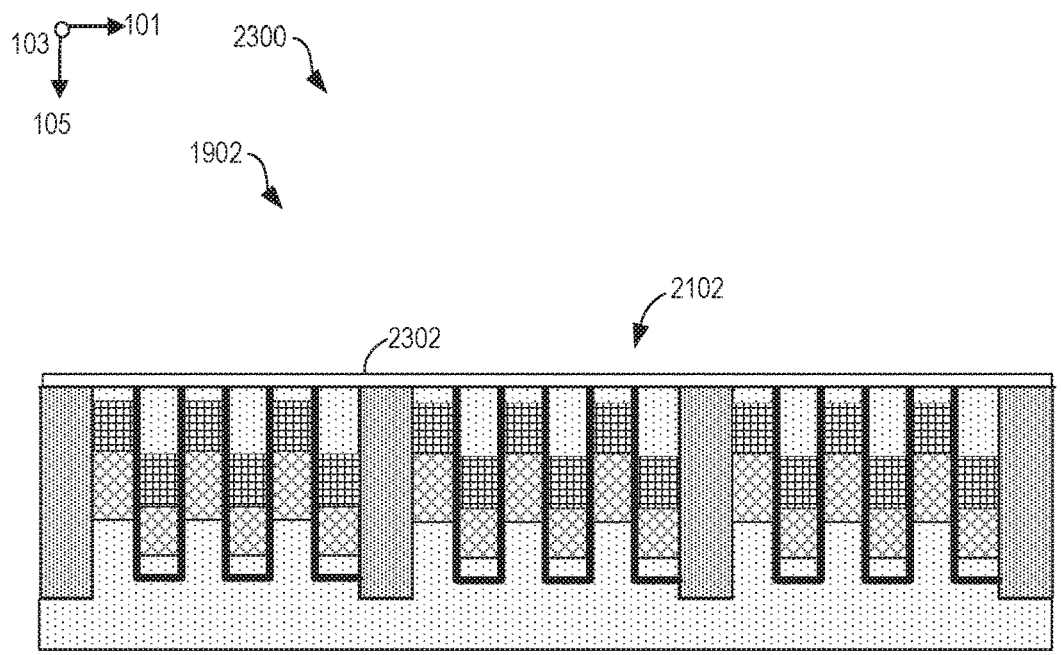
FIG. 23 shows the fourth example of the acoustic stack block with a conductive layer coupled to the ground back side, viewed along the elevation direction.
Figure 24:
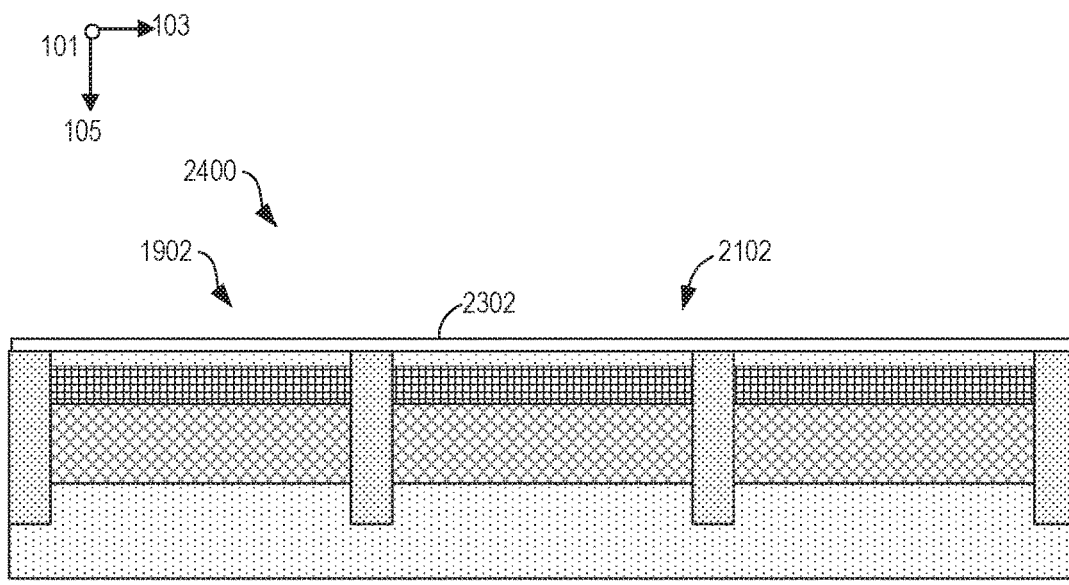
FIG. 24 shows the fourth example of the acoustic stack block with the conductive layer coupled to the ground back side, viewed along the azimuth direction.

Ground recovery may further include sputtering a layer of an electrically conductive material, such as a metal, on the back side 2102 of the fourth acoustic stack 1902, as shown in FIG. 23 in a first view 2300 along the elevation direction 103 and in FIG. 24 in a second view 2400 along the azimuth direction 101. The fourth acoustic stack 1902 is depicted in FIGS. 23 and 24 flipped upside, relative to the azimuth direction 101. A sputtered layer 2302 is deposited onto the back side 2102 of the fourth acoustic stack 1902, forming a uniform, continuous film. A height, measured along the azimuth direction, of the sputtered layer 2302 is less than the heights of the any of other layers, e.g., the matching layers, the high and low frequency elements, the dematching layers, the backing layers, of the fourth acoustic stack 1902.

In other examples, however, sputtering may be precluded by grinding the back side of the fourth acoustic stack 1902 to a lesser extent, so that a portion of the base package 1602 remains. For example, the back side may be ground by an amount indicated by arrow 1907 shown in FIG. 19. The remaining portion of the base package may be common to each of the sub-elements and may provide an electrically conductive layer along the backside of the fourth acoustic stack 1902.

Figure 25:
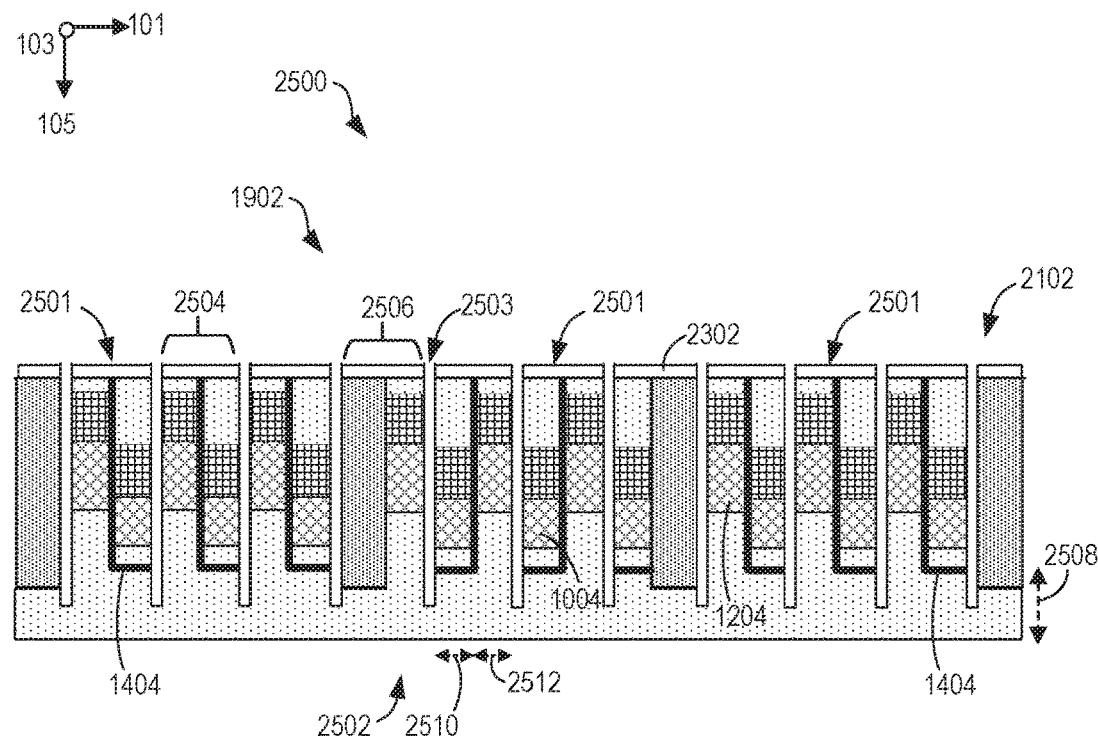
FIG. 25 shows a dicing of the fourth example of the acoustic stack block, viewed along the elevation direction.
Figure 26:
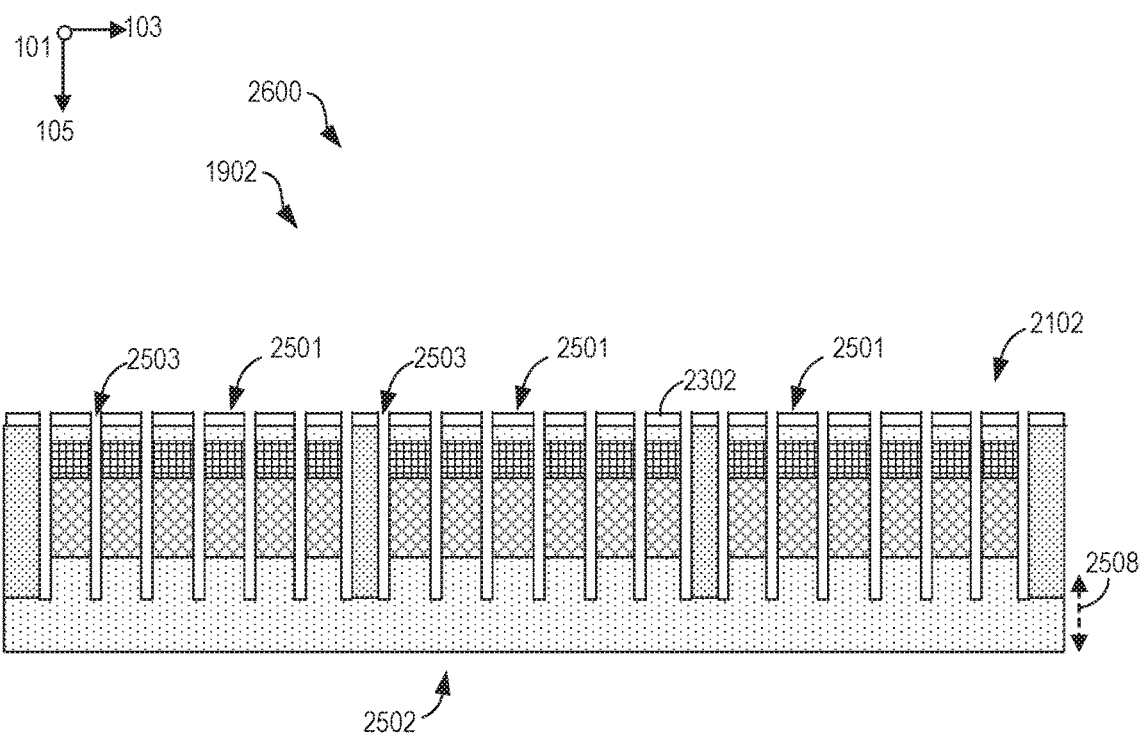
FIG. 26 shows the dicing of the fourth example of the acoustic stack block, viewed along the azimuth direction.

The fourth acoustic stack 1902 may be diced after deposition of the sputtered layer 2302, as shown in FIG. 25 in a first view 2500 of the fourth acoustic stack 1902 along the elevation direction 103 and in FIG. 26 in a second view 2600 along the azimuth direction 101. A plurality of kerfs 2503 are formed in the fourth acoustic stack 1902, extending from the back side 2302 towards a front side 2502 of the fourth acoustic stack 1902 but not entirely through the fourth acoustic stack 1902, along the transverse direction 105.

The plurality of kerfs 2503 may separate the fourth acoustic stack 1902 into a plurality of elements 2501. The plurality of elements 2501 may include multi-frequency elements 2504 and single frequency elements 2506, as shown in FIG. 25. The multi-frequency elements 2504 each include one of the high frequency sub-elements 1004 and one of the low frequency sub-elements 1204. The single frequency elements 2506 include either one of the high frequency sub-elements 1004 or one of the low frequency sub-elements 1204 but not both.

In other examples, each element of an acoustic stack, such as the fourth acoustic stack 1902, may be formed from a single element but the acoustic stack may include various different types of single elements. For example, a first and second comb structure may be combined to form a similar acoustic stack as the third acoustic stack 1402 of FIGS. 14-15. The acoustic stack may be processed as described above with reference to FIGS. 16-24, and kerfs may be diced into the acoustic stack, as shown in FIGS. 25 and 26. However, the kerfs may be positioned between each fin of each comb structure, thus separating the elements into single element digits of the diced acoustic stack. In other words kerfs may also separate the high frequency sub-elements 1004 from the low frequency sub-elements 1204. In this way, the acoustic stack may be a multi-frequency acoustic stack with single elements, rather than elements formed from more than one sub-element, where each transducer may have more than one type of element, each element coupled to an electrical circuit.

Returning to FIG. 25, a resonance frequency of the multi-frequency elements 2504 may be determined by a percent content of each of the high and low frequency sub-elements 1004, 1204. A first width 2510, defined along the azimuth direction 101, of the high frequency sub-element 1004 is similar to a second width 2512 of the low frequency sub-element 1204. As such the multi-frequency elements 2504 may each be formed of 50% of the high frequency sub-element 1004 and 50% of the low frequency sub-element 1204 and have a resonance frequency mid-way between that of the high frequency sub-element 1004 and the low frequency sub-element 1204. In other examples, however, the widths of the sub-elements may be varied, e.g., not equal, and may be non-uniform throughout an acoustic stack, resulting in a range of resonance frequencies. Variations in sub-element widths are depicted in FIGS. 31-34 and described further below.

Figure 27:
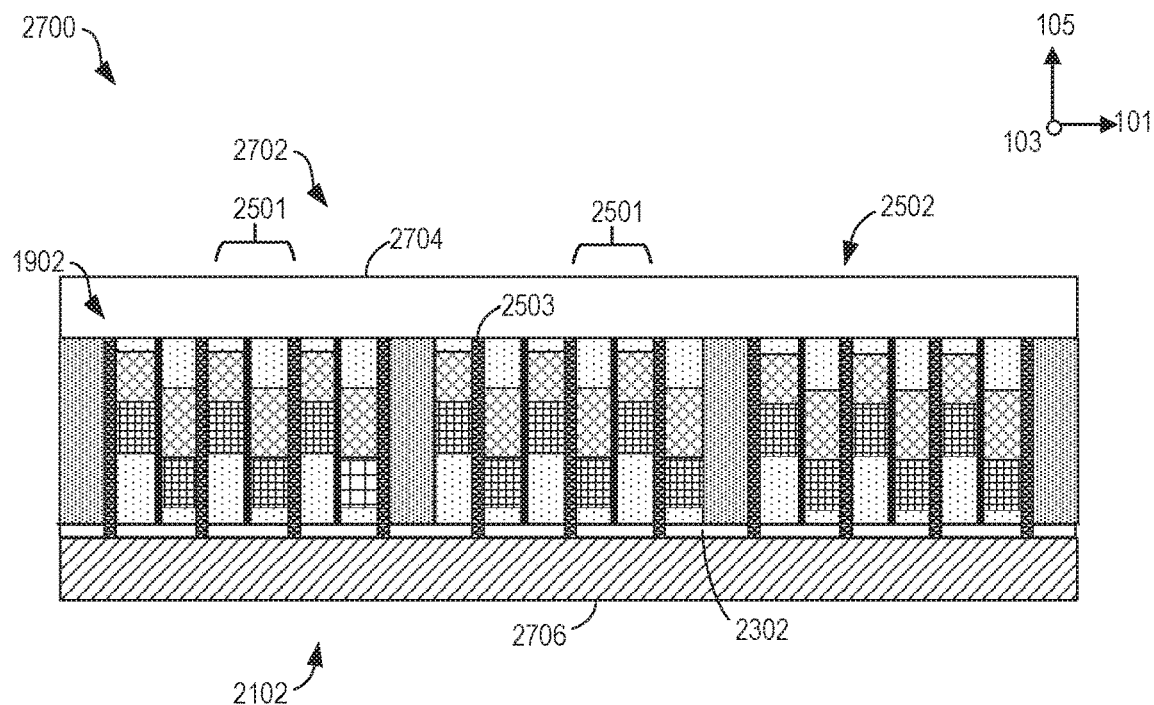
FIG. 27 shows a coupling of a matching layer block to a front side and a backing layer block to a back side of the fourth example of the acoustic stack block, viewed along the elevation direction.
Figure 28:
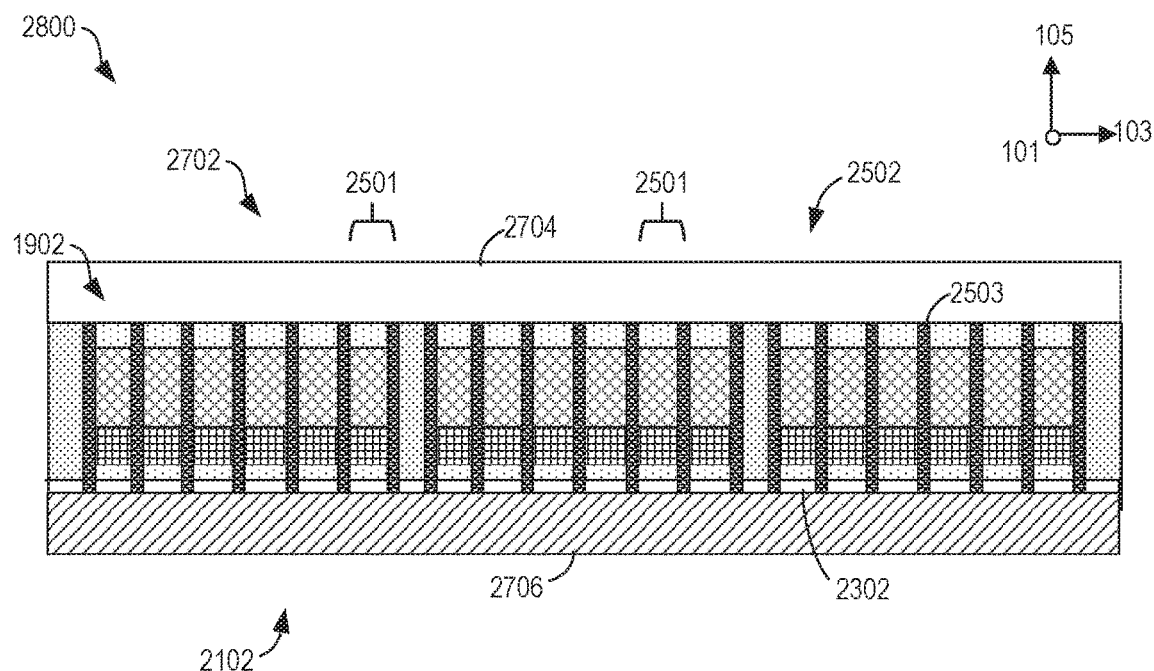
FIG. 28 shows the coupling of the matching layer block to the front side and the backing layer block to the back side of the fourth example of the acoustic stack block, viewed along the azimuth direction.

The plurality of kerfs 2503 may be filled with an electrically insulating material, thereby insulating each of the plurality of elements 2501 from adjacent elements. However, in other examples the plurality of kerfs 2503 may be maintained as air-filled spaces (e.g., not filled with any additional materials), which may similarly provide electrical insulation. Furthermore, maintaining the plurality of kerfs 2503 as spaces may reduce an overall amount of material of the transducer array and reduce a weight of the array. The filled plurality of kerfs 2503 are depicted in FIG. 27 in a first view 2700 along the elevation direction 103 and in FIG. 28 in a second view 2800 along the azimuth direction 101. The fourth acoustic stack 1902 is shown incorporated in a wafer 2702 in FIGS. 27 and 28.

In addition to filling the plurality of kerfs 2503, a portion of the front side 2502 of the fourth acoustic stack 1902 may be mechanically removed, similar to the grinding of the back side 2102, to further enable ground recovery. The front side 2502 of the fourth acoustic stack 1902 may provide electrical grounding. A height 2508 of the portion of the fourth acoustic stack 1902 that is removed from the front side 2502 is shown in FIGS. 25 and 26. The amount ground away from the front side 2502 of the fourth acoustic stack 1902 may remove portions of the first layer of adhesive 1404 parallel with the azimuth direction 101, as shown in FIG. 25. Grinding of the front side 2502 may also contribute to ground recovery in the azimuth and elevation directions by enabling electrical continuity between the plurality of elements 2501 and an electrically conductive layer coupled to the front side 2502 of the fourth acoustic stack 1902, described further below.

Returning to FIGS. 27 and 28, a matching layer block 2704 is laminated to the front side 2502 of the fourth acoustic stack 1902 after grinding. Although not depicted in FIGS. 27 and 28, in some examples, a conductive layer, such as the sputtered layer 2302, may be sputtered onto the ground front side 2502 of the fourth acoustic stack 1902 before coupling the matching layer block 2704 to the front side 2502. The matching layer block 2704 may be laminated using a conductive adhesive and may be a same or different material as the matching layers 1002, 1202 of the first comb structure 1100 and the second comb structure 1300, respectively. For example, the material of the matching layer block 2704 may be a gold-coated material, flex conductive materials such as a spring mass structure, etc. The matching layer block 2704 may be formed of more than layer and may be formed of an electrically conductive material or a non-conductive material.

The matching layer block 2704 provides a common matching layer to each transducer of the fourth acoustic stack 1902, each transducer including one of the plurality of elements 2501 and defined along the transverse direction 105 by the plurality of kerfs 2503, filled with the non-conductive material. In other words, the matching layer block 2704 is a continuous layer that extends entirely across the front side 2502 of the fourth acoustic stack 1902. Similarly, a backing layer block 2706 may be coupled to the back side 2102 of the fourth acoustic stack 1902, and connected to each transducer of the fourth acoustic stack 1902 to provide a common backing layer for each transducer. The backing layer block 2706 may also be a continuous layer that extends entirely across the back side 2102 of the fourth acoustic stack 1902.

A backing layer block 2706 may be laminated to the back side 2102 of the fourth acoustic stack 1902 to form the wafer 2702, also using a conductive adhesive. The backing layer block 2706 may be formed of one or more layers, laminated in a stack along the transverse direction 105, and may provide an electrical path to enable application of a voltage to the plurality of elements 2501. In some examples, the backing layer block 2706 may include an application specific integrated circuit (ASIC), a flex conductive material, a printed circuit board (PCB), a metal block, etc. In other examples, a backing of some type may be coupled to the back side 2102 of the fourth acoustic stack 1902 instead of the backing layer block 2706. For example, the backing may be an interposer connecting a flex circuit to the acoustic stack.

In addition, other examples may include the acoustic stack configured with non-continuous matching and backing layer blocks that do not extend continuously across each transducers. For example, a plurality of smaller matching and backing layer blocks may be coupled to a transducer array, each block attached to one transducer. Alternatively, the matching and backing layer blocks may cover a few transducers, such as two or three adjacent transducers, coupling to the acoustic stack in segments.

Figure 29:
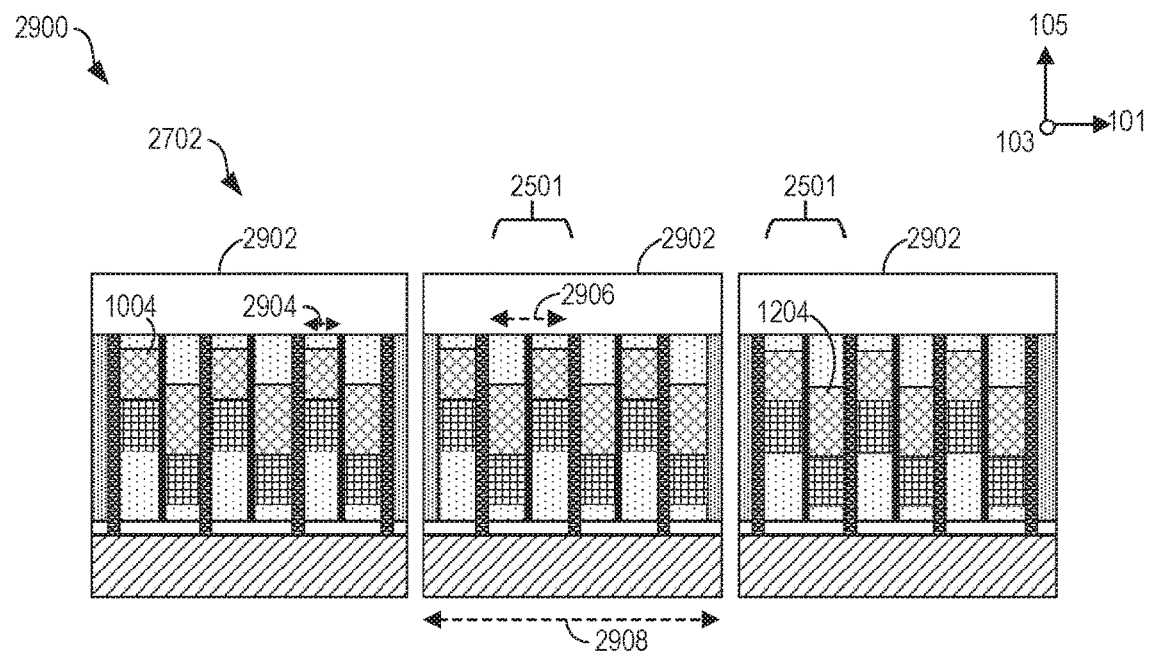
FIG. 29 shows singulation of the fourth example of the acoustic stack block, viewed along the elevation direction.
Figure 30:
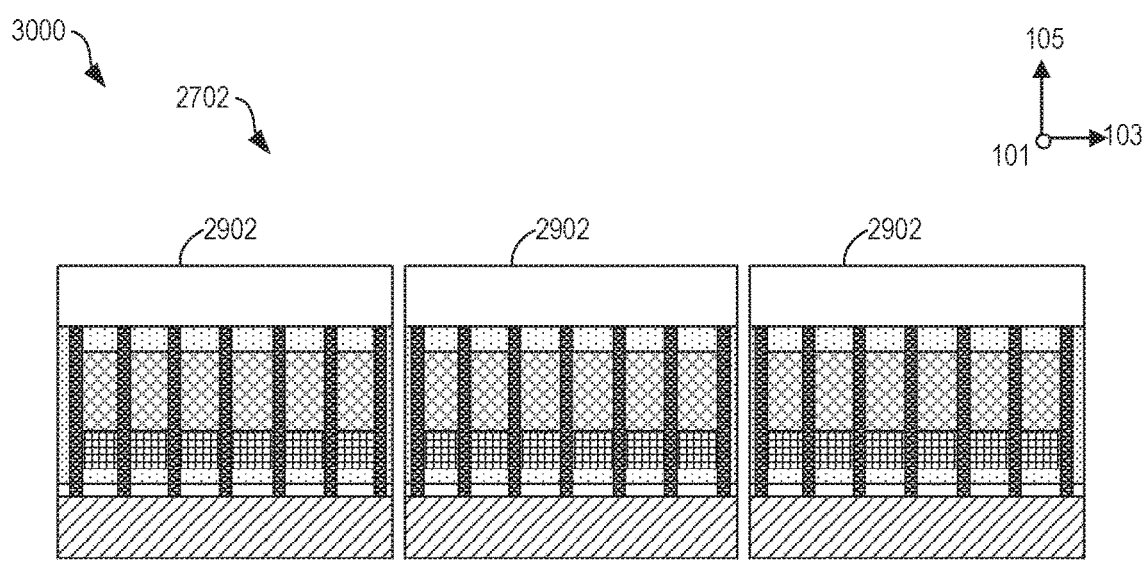
FIG. 30 shows singulation of the fourth example of the acoustic stack block, viewed along the azimuth direction.
Figure 31:
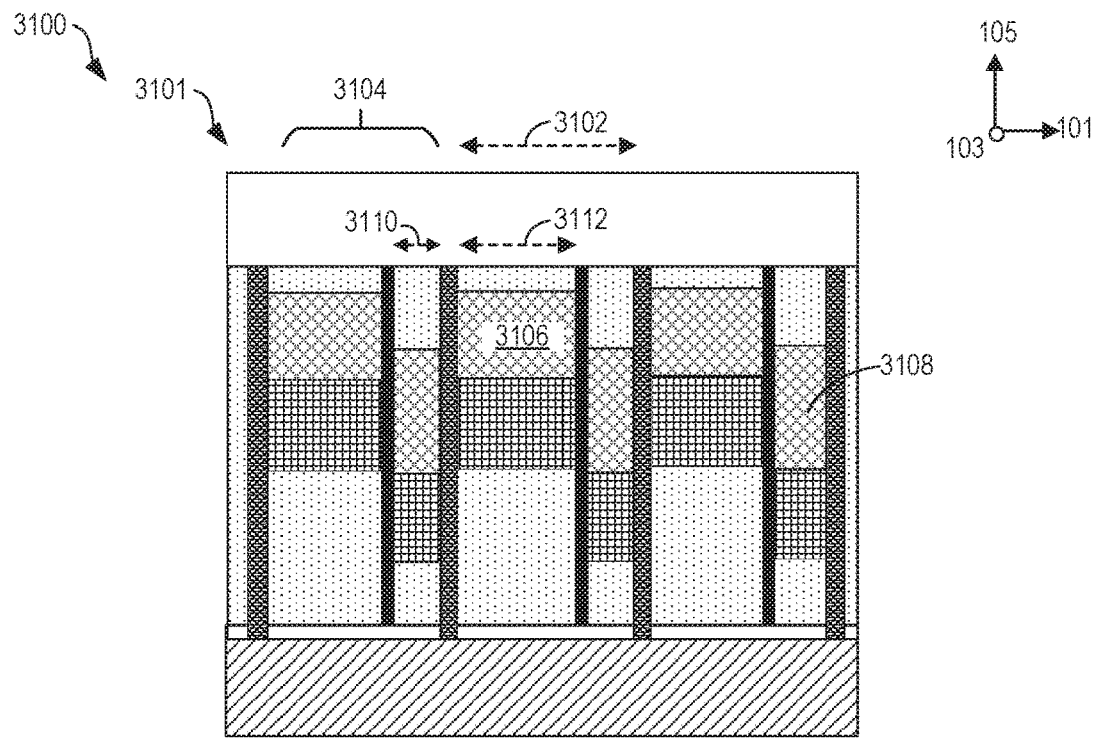
FIG. 31 shows a fifth example of a multi-element acoustic stack.
Figure 32:
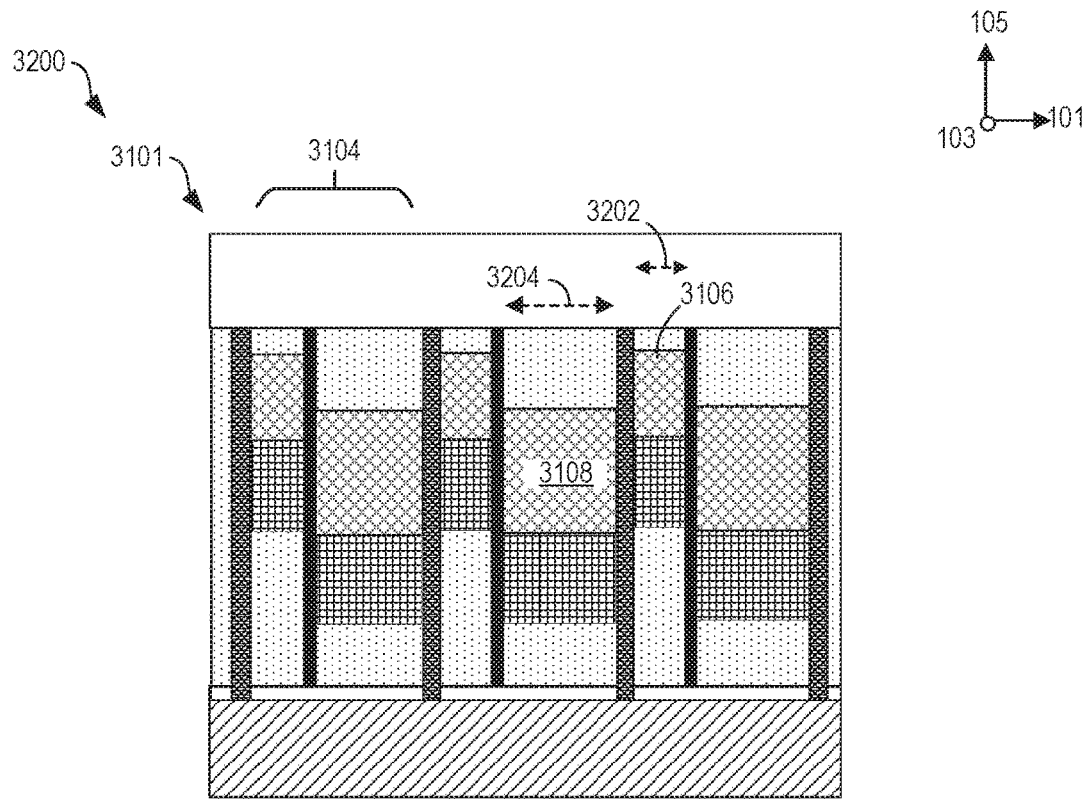
FIG. 32 shows a sixth example of a multi-element acoustic stack.
Figure 33:
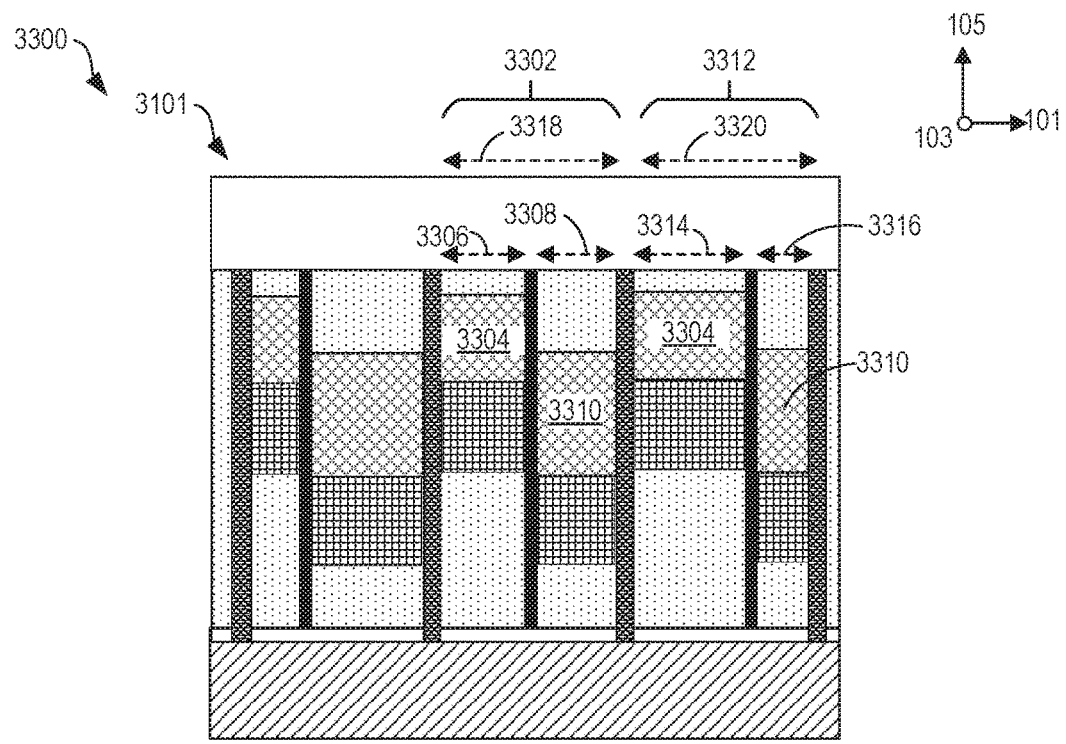
FIG. 33 shows a seventh example of a multi-element acoustic stack.
Figure 34:
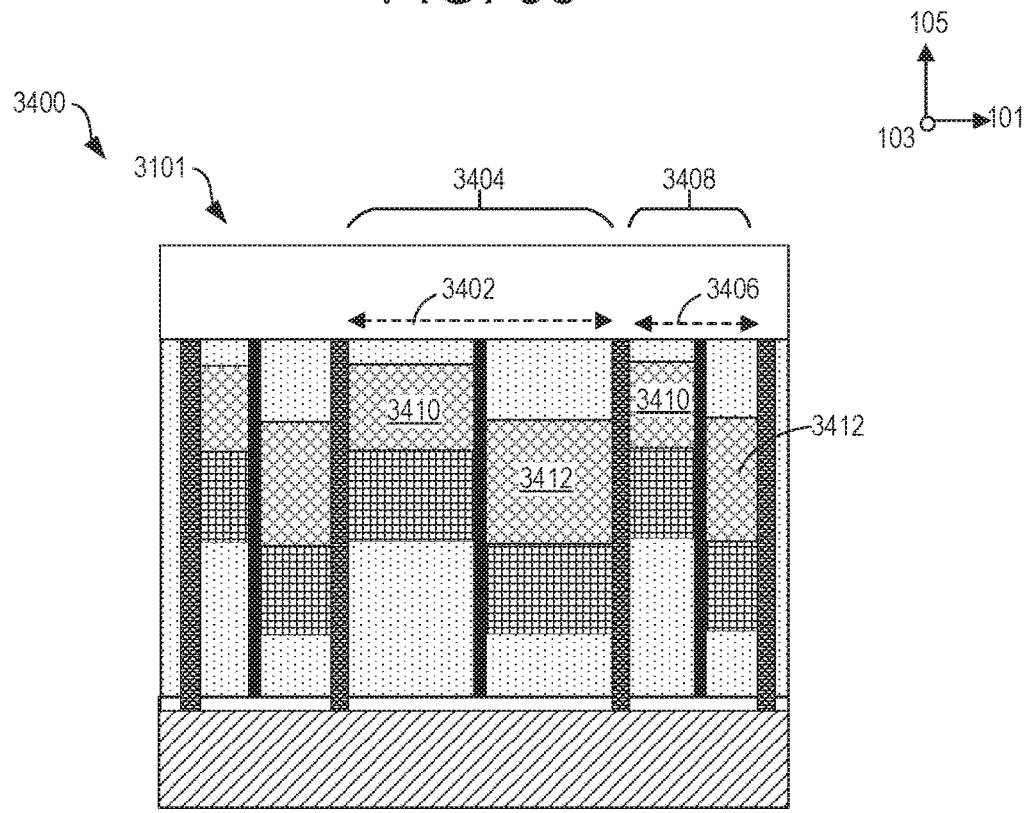
FIG. 34 shows an eighth example of a multi-element acoustic stack.

The wafer 2702 may then be singulated, e.g., singularized, to form individual transducer arrays 2902, as shown in FIG. 29 in a first view 2900 along the elevation direction 103 and in FIG. 30 in a second view 3000 along the azimuth direction 101. Each of the transducer arrays 2902 includes an array of the plurality of elements 2501, each of the plurality of elements 2501 included in an individual integrated circuit. Singulation may include various methods of die singulation, including conventional dicing, laser dicing, scribe and break, and dice before grind. Each of the transducer arrays 2902 are therefore spaced away from neighboring transducer arrays as a result of singulation and each transducer may be installed in a transducer probe.

Although a width 2904, defined along the azimuth direction 101, of each of sub-elements (e.g., the high frequency sub-element 1004 and the low frequency sub-elements 1204), a width 2906 of each of the plurality of elements 2501, as well as a width 2908 of each of the transducer arrays 2902 is depicted to be uniform in FIG. 29, the dicing of each of the above components of the wafer 2702 may be modified to produce non-uniform widths. Variations in widths of the sub-elements, of the plurality of elements, and of the transducers are shown in FIGS. 31-35.

In a first example 3100 of a non-uniform transducer array 3101, a width 3102 of a plurality of elements 3104 may be uniform along the azimuth direction 101. The plurality of elements 3104 may each include a first sub-element 3106 and a second sub-element 3108. A first comb structure may be diced to form the first sub-element 3106 with a width 3110 that is greater than a width 3112 of the second sub-element 3108. In other words the first comb structure may be diced to form wider sub-elements (e.g., the first sub-elements 3106) than dicing of a second comb structure to form the second sub-element 3108.

Alternatively, as shown in a second example 3200 of the non-uniform transducer array 3103, the first comb structure may be diced so that the first sub-element 3106 has a narrower width 3202 than a width 3404 of the second sub-element 3108, formed by dicing of the second comb structure. The width 3104 of each of the plurality of elements 3104 may be uniform along the azimuth direction 101 and the widths of each of the first sub-element 3106 and of the second sub-element 3108 may be similar in each of the plurality of elements 3104. Thus the widths of the sub-elements may be readily varied based on dicing of the comb structures.

Furthermore, the comb structures may be diced so that each of the sub-elements have non-uniform widths, as shown in a third example 3300 of the non-uniform transducer array 3101. A first element 3302 may be formed of a first sub-element 3304 with a width 3306 that is similar to a width 3308 of a second sub-element 3310. However, in a second element 3312, adjacent to the first element 3302, a width 3314 of the first sub-element 3304 is greater than a width 3316 of the second sub-element 3310. A width 3318 of the first element 3302 may be similar to a width 3320 of the second element 3312. In other examples, the non-uniform transducer array 3103 may include elements where the width of the second sub-element 3310 is greater than the width of the first sub-element 3304.

Additionally or alternatively, dicing of an acoustic stack formed by combining the first and second comb structures, e.g., the third acoustic stack 1402 of FIGS. 14-17, may be modified to vary a width of the plurality of elements. For example, as shown in a fourth example 3400 of the non-uniform transducer array 3101, a width 3402 of a first element 3404 may be greater than a width 3406 of a second element 3408. Widths of a first sub-element 3410 and a second sub-element 3412 of each of the elements may be similar, as shown in the first element 3404, or different, as shown in the second element 3408.

Figure 35:
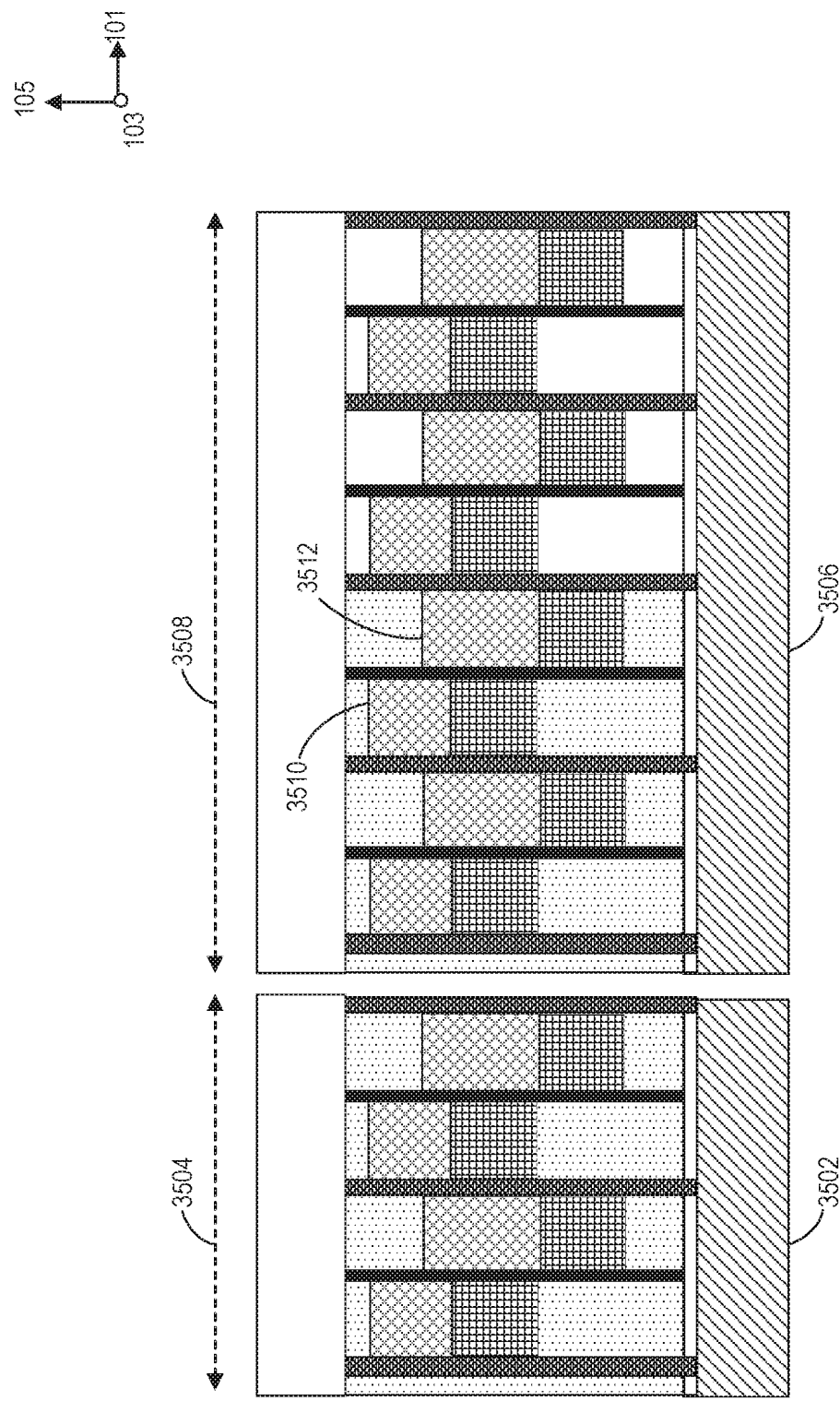
FIG. 35 shows a variation in dicing of the fourth example of the acoustic stack block of FIGS. 29 and 30.

Furthermore, singulation of a wafer into individual transducer arrays may be adjusted to form transducers of varying widths. As illustrated in FIG. 35, a first transducer array 3502 may be diced to have a first width 3504. A second transducer array 3506 may be diced to have a second width 3508 that is wider than the first width 3504 of the first transducer array 3502. Other transducer arrays formed from the same wafer as the first and second transducer arrays 3502, 3506 may have widths similar to either the first transducer array 3502 or the second transducer array 3506 or widths that are different from either of the first and second transducer arrays 3502, 3506. Widths of a first sub-element 3510 and a second sub-element 3512 incorporated in each of the elements of each transducer array may be similar to one another or different and may be uniform or non-uniform through the transducer array.

Electrical leads may be coupled to the matching layer block and the backing layer block of the transducers array before or after singulation. For example, positive electrodes may be coupled to the matching layer block and ground electrodes may be coupled to the backing layer block. Alternatively, the positive electrodes may be coupled to the backing layer block and the ground electrodes may be coupled to the matching layer block. Formation of individual circuits with each transducer is thereby completed by coupling the transducers arrays to electrical leads.

In this way, a manufacturing method for multi-frequency transducers may be fabricated to produce multi-frequency elements and transducer arrays as shown in FIGS. 2 and 4-36. It will be appreciated that while FIGS. 31-35 depict views of the transducers(s) along the elevation direction 103 and describe variations in widths of the transducer(s), elements, and sub-elements relative to the elevation direction 103, similar variations may be applied along the azimuth direction 101. For example, dicing of the comb structures may be modified along the azimuth direction 101 to provide sub-elements with varying depths (e.g., a thickness of the sub-elements along the azimuth direction 101). The comb structures may be combined so that the sub-elements are arranged adjacent to one another along the azimuth direction 101, instead of or in addition to arrangement of the sub-elements next to one another along the elevation direction 103.

A combined comb structure may be diced to generate elements of varying depths along the azimuth direction 101 while also varying widths of the elements along the elevation direction 103. Alternatively, the widths of the elements may be maintained uniform along the elevation direction 103 and varied along the azimuth direction 101. Furthermore, depths of the singulated transducers may similarly be varied along the azimuth direction 101 in addition to or instead of along the elevation direction 103.

By enabling dimensions of the transducers, elements, and sub-elements to be varied along both the azimuth direction 101 and elevation direction 103, scalable fabrication of the transducers is enabled. A variety of transducers with different and broad bandwidths and spatial frequency distribution may be produced from a single wafer. Electrical circuits are coupled to the wafer prior to singulation, increasing an efficiency of manufacturing. A quantity of interconnects and control signals in a multi-frequency transducer probe may be similar to a quantity used in a single-frequency transducer probe. Thus, implementation of multi-frequency transducer arrays does not introduce additional complexity to transducer probes.

Ground recovery along both the elevation and azimuth directions allows greater flexibility in packaging of a transducer array in a probe. For example, a transducer array with a reduced footprint in the elevation direction may be desirable. In conventional methods, ground recovery may be difficult when the transducer array is shortened along the elevation direction. The fabrication process described above with reference to FIGS. 10-38 and 40-42, however, allows for ground recovery along the azimuth direction instead. Additionally, an apodization function provided by the spatial frequency distribution of the broad bandwidth transducers may allow a transducer probe to be used for more than one application. For example, a single transducer probe may be used for both therapy and imaging. Image quality may be optimized in both near and far fields due to an enhanced beam focus profile enabled by the apodization function. A footprint of the transducer probe may be optimized for more efficient packaging. As well, a manufacturing process of an acoustic stack of the transducer probe, as illustrated in FIGS. 10-36 may provide a universal architecture, based on a collective wafer approach, applicable to all transducer portfolios.

An example of a first routine 3700 for fabricating a multi-frequency acoustic stack for a transducer probe is depicted in FIG. 37. A second routine 3800, as shown in FIG. 38, is an example of a routine for forming multi-frequency elements which may be included in the first routine 3700. The first and second routines 3700, 3800 describe a process similar to the manufacturing process illustrated in FIGS. 10-36. Turning now to FIG. 37, at 3702, the first routine 3700 includes forming a first acoustic stack, as shown in the second routine 3800 in FIG. 38.

At 3802 of FIG. 38, the second routine 3800 includes forming a first comb structure, such as the first comb structure 1100 of FIG. 11, which has a first sub-element. The first comb structure may be formed by dicing a first acoustic stack, such as the first acoustic stack 1000 of FIG. 10. A second comb structure is formed at 3804, such as the second comb structure 1300 of FIG. 13, which has a second sub-element with a different resonance frequency than the first sub-element. The second comb structure may be formed by dicing a second acoustic stack, such as the second acoustic stack 1200 of FIG. 12. Both the first acoustic stack and the second acoustic stack may each include a matching layer, a sub-element layer, an optional dematching layer, and a backing layer, the layers stacked along a transverse direction perpendicular to both an azimuth direction and an elevation direction.

The first acoustic stack and the second acoustic stack may be diced along opposite directions from one another to impart the first and second comb structures with complementary fins. For example, as shown in FIG. 11, the first acoustic stack may be diced downwards from a top surface of the first acoustic stack and, as shown in FIG. 13, the second acoustic stack may be diced upwards from a bottom surface of the second acoustic stack. Alternatively, the first acoustic stack may be diced upwards from a bottom surface while the second acoustic stack may be diced downwards from a top surface.

At 3806, the first comb structure is combined with the second comb structure to form an interdigitated combined stack, such as the third acoustic stack 1402 of FIG. 14. The combined stack may be laminated to adhere the comb structures to one another.

At 3808, the routine includes determining if an additional sub-element is to be incorporated into the combined stack. If no additional sub-element is to be included, the routine continues to 3704 of the first routine 3700 of FIG. 37. If at least one additional sub-element is to be incorporated, an additional comb structure is formed at 3810. The additional comb structure may be diced similar to the first comb structure 1100 of FIG. 11 or the second comb structure 1300 of FIG. 13 while the combined stack may be diced at 3812 in an opposite manner to complement a geometry of the diced additional comb structure. The additional comb structure may have a third sub-element with a different resonance frequency than the first or second sub-elements.

In some examples, the additional comb structure may be a combined comb structure, formed via a similar process as described in 3802-3806 of the second routine 3800, so that the additional comb structure has a fourth sub-element in addition to the third sub-element. The additional comb structure with both the third and fourth sub-elements may be similarly diced to have a complementary geometry to the diced combined stack.

At 3814, the second routine 3800 includes combining the diced combined stack with the additional comb structure to form a new combined stack which may be laminated to adhere the combined stack and the additional comb structure to one another. During lamination, a layer of non-conductive adhesive may be disposed between the first and second comb structures. The method returns to 3808 to again determine if an additional sub-element is to be incorporated into the (new) combined stack.

Returning to FIG. 37, at 3704 of the first routine 3700, the first acoustic stack, e.g., the combined stack formed via the second routine 3800, is diced. Dicing of the first acoustic stack forms a plurality of fins separated by a plurality of kerfs in the first acoustic stack. At 3706, a base package formed of a conductive material, such as the base package 1602 of FIG. 16, is diced to have fins with a similar geometry to the plurality of kerfs in the first acoustic stack and kerfs with a similar geometry to the plurality of fins in the first acoustic stack.

The base package and the first acoustic stack are coupled to one another and laminated at 3708 to form a second acoustic stack. At 3710, a portion of a back side of second acoustic stack may be removed by grinding to provide ground recovery. For example, a portion of a thickness of a backing layer of the first acoustic stack, as well as portions of the non-conductive adhesive used to laminate the first acoustic stack, may be removed. By removing a part of the backing layer and the portions of the non-conductive adhesive, ground recovery along the azimuth and elevation directions may be enabled.

At 3712, a conductive layer is sputtered on the ground back side of the second acoustic stack. The conductive layer may allow electrical connections to be coupled to the back side of the second acoustic stack, each of the electrical connections included in an integrated circuit of a final transducer array formed via processing of the second acoustic stack. The second acoustic stack is diced at 3714 and kerfs formed by dicing may be filled with a non-conductive material, thereby electrically insulating each integrated circuit, or transducer, of the second acoustic stack from adjacent integrated circuits.

A front side of the second acoustic stack is ground at 3716. The front side is opposite of the back side and a portion of a thickness of the front side may be removed by grinding. For example, a matching layer of the second acoustic stack may be partially removed. At 3718, a matching layer block and a backing layer block may be coupled to the front and back sides, respectively, of the second acoustic to further enable ground recovery in the azimuth and elevation directions. At 3720, the first routine 3700 includes singulating the second acoustic stack to divide the second acoustic stack into separate transducer arrays. The transducer arrays may each be implemented in a transducer probe. The first routine 3700 ends.

In this way, a multi-element transducer array may be provided for a transducer probe. The multi-element transducer array may include sub-elements with different resonance frequencies, distributed along the azimuth and elevation directions in a homogeneous pattern. Alternatively, the sub-elements may positioned to provide varying spatial frequency distributions along at least one of the azimuth and elevations directions. Frequency apodization and agility is enabled along the elevation direction and on different structures, e.g., 1D, 1.5D, 2D, etc, enabling spatial frequency distribution in complex structures. Furthermore, frequency apodization and agility is achieved at low cost by fabricating the multi-element transducer through a wafer scale approach. A processing of an acoustic stack during the wafer scale approach may result in a large distribution of frequency content over a transducer aperture that allows one transducer probe to be use for multiple applications. Image quality may be optimized in both a near and far field due to a beam focus profile enabled by frequency apodization. The multi-element transducer array may be packaged more efficiently within the transducer probe due to ground recovery in both the azimuth and elevation directions and may be used in a variety of transducer portfolios.

The technical effect of fabricating the transducer array via the wafer scale approach is that a broad bandwidth transducer array is produced via a cost efficient method. Another technical effect is that frequency apodization and agility is enabled along the azimuth and elevation directions.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

In one embodiment, a method includes forming a first comb structure with a first sub-element having a first resonance frequency, forming a second comb structure, complementary in geometry to the first comb structure with a second sub-element having a second resonance frequency, combining the first and second comb structures to form an interdigitated structure, forming a third acoustic stack by coupling the interdigitated structure to a base package, and coupling the third acoustic stack to a matching layer block and a backing layer block to form a plurality of multi-frequency transducers. In a first example of the method, forming the first comb structure from a first acoustic stack, the first acoustic stack having a first matching layer, the first sub-element, and a first backing layer and forming the second comb structure from a second acoustic stack, the second acoustic stack having a second matching layer, the second sub-element, and a second backing layer and wherein the first and second matching layers include one or more layers configured to be electrically conductive along a vertical axis of the first and second acoustic stacks. A second example of the method optionally includes the first example, and further includes, wherein forming the first comb structure includes dicing a first set of kerfs into the first acoustic stack to form a first set of fins, the first set of kerfs extending downwards from a top surface of the first acoustic stack and wherein forming the second comb structure includes dicing a second set of kerfs into the second acoustic stack to form a second set of fins, the second set of kerfs extending upwards from a bottom surface of the first acoustic stack. A third example of the method optionally includes one or more of the first and second examples, and further includes, wherein forming the first and second comb structures further includes forming the first set of fins of the first comb structure with dimensions to allow the first set of fins to be inserted into the second set of kerfs of the second comb structure and forming the second set of fins of the second comb structure with dimensions to allow the second set of fins to be inserted into the first set of kerfs of the first comb structure. A fourth example of the method optionally includes one or more of the first through third examples, and further includes, wherein dicing the first set of kerfs into the first acoustic stack and dicing the second set of kerfs into the second acoustic stack includes configuring the first and second sets of kerfs with a non-uniform dimension along at least one of an azimuth and an elevation direction. A fifth example of the method optionally includes one or more of the first through fourth examples, and further includes, wherein forming the first and second acoustic stacks includes dicing the acoustic stacks so that at least one of the first set of kerfs and the second set of kerfs are non-uniformly spaced apart along at least one of an azimuth and an elevation direction. A sixth example of the method optionally includes one or more of the first through fifth examples, and further includes dicing the interdigitated structure prior to coupling the interdigitated structure to the base package and coupling the diced interdigitated structure to a third comb structure. A seventh example of the method optionally includes one or more of the first through sixth examples, and further includes, wherein coupling the diced interdigitated structure to the third comb structure incorporates at least one additional sub-element with a different resonance frequency from either of the first and second sub-elements into the interdigitated structure. An eighth example of the method optionally includes one or more of the first through seventh examples, and further includes dicing the interdigitated structure a number times equal to a number of additional sub-elements to be incorporated into the interdigitated structure. A ninth example of the method optionally includes one or more of the first through eighth examples, and further includes, wherein dicing the interdigitated structure includes cutting kerfs into the interdigitated structure that are uniformly spaced apart and wherein the third comb structure also has uniformly spaced apart kerfs and a geometry complementary to a geometry of the diced interdigitated structure. A tenth example of the method optionally includes one or more of the first through ninth examples, and further includes, wherein dicing the interdigitated structure includes cutting kerfs into the interdigitated structure that are non-uniformly spaced apart and wherein the third comb structure also has non-uniformly spaced apart kerfs and a geometry complementary to a geometry of the diced interdigitated structure.

In another embodiment, a method includes combining two or more comb structures into a single acoustic stack to incorporate two or more sub-elements with different resonance frequencies, separating the single acoustic stack into transducer arrays, each of the transducer arrays including at least one transducer, and varying a distribution of the two or more sub-elements along at least one of an azimuth and an elevation direction to have frequency apodization and frequency agility. In a first example of the method, separating the single acoustic stack into transducer arrays includes singularizing the single acoustic stack to divide the single stack into the transducer arrays. A second example of the method optionally includes the first example, and further includes providing a common ground for the transducer arrays by coupling the acoustic stack to a base package electrically coupled to each of the transducers and wherein each of the transducers includes a piezoelectric element formed from the two or more sub-elements. A third example of the method optionally includes one or more of the first and second examples, and further includes forming an individual integrated circuit with each piezoelectric element. A fourth example of the method optionally includes one or more of the first through third examples, and further includes, wherein varying the distribution of the two or more sub-elements includes incorporating at least one of the two or more sub-elements into each transducer. A fifth example of the method optionally includes one or more of the first through fourth examples, and further includes, wherein varying the distribution of the two or more sub-elements includes varying relative proportions of the two or more sub-elements in each transducer. A sixth example of the method optionally includes one or more of the first through fifth examples, and further includes, wherein separating the single acoustic stack into transducer arrays includes forming transducer arrays with any of a linear, a curved linear, and a matrix-like arrangement.

In yet another embodiment, a transducer array includes a plurality of transducers, each transducer incorporated into an individual electronic circuit and including a piezoelectric element formed from one or more sub-elements and wherein a distribution of the one or more sub-elements amongst the plurality of transducers is varied along at least one of an azimuth and an elevation direction. In a first example of the transducer array, at least one of the one or more sub-elements has a different resonance frequency and wherein the one or more sub-elements are incorporated into each transducer via a wafer scale approach.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A multi-frequency transducer array, comprising: a plurality of piezoelectric elements, a piezoelectric element of the plurality formed from at least two sub-elements in face-sharing contact, the at least two sub-elements having different resonance frequencies, and wherein a distribution of the at least two sub-elements is varied along at least one of an azimuth and an elevation direction.

2. The multi-frequency transducer array of claim 1, wherein the piezoelectric elements are a PZT type, and wherein the distribution includes at least one piezoelectric element with more than 50% of a first sub-element type and less than 50% of a second sub-element type, 50% of the first sub-element type and 50% of the second sub-element type, and less than 50% of the first sub-element type and more than 50% of the second sub-element type.

3. The multi-frequency transducer array of claim 2, wherein a first comb structure of a first sub-element has a first resonance frequency; a second comb structure complementary in geometry to the first comb structure with a second sub-element has a second resonance frequency, wherein the first and second comb structures are combined to form an interdigitated structure.

4. The multi-frequency transducer array of claim 3, wherein the first comb structure is formed from a first acoustic stack, the first acoustic stack having a first matching layer, the first sub-element, and a first backing layer, and the second comb structure is formed from a second acoustic stack, the second acoustic stack having a second matching layer, the second sub-element, and a second backing layer, and wherein the first and second matching layers include one or more layers configured to be electrically conductive along a vertical axis of the first and second acoustic stacks.

5. The multi-frequency transducer array of claim 4, wherein a first set of kerfs is diced into the first acoustic stack to form a first set of fins, the first set of kerfs extending downwards from a top surface of the first acoustic stack and a second set of kerfs is diced into the second acoustic stack to form a second set of fins, the second set of kerfs extending upwards from a bottom surface of the first acoustic stack.

6. The multi-frequency transducer array of claim 3, wherein the interdigitated structure is diced prior to coupling the interdigitated structure to the base package, and the diced interdigitated structure is coupled to a third comb structure.

7. The multi-frequency transducer array of claim 1, wherein at least one sub-element is single crystal.

\* \* \* \* \*